(12) United States Patent
Metzger et al.

(10) Patent No.: US 9,598,488 B2
(45) Date of Patent: Mar. 21, 2017

(54) BLOCKAGE OF INTERFERON-GAMMA FOR PREVENTION OF POLYMICROBIAL SYNERGY

(75) Inventors: Dennis W. Metzger, Niskayuna, NY (US); Keer Sun, Latham, NY (US)

(73) Assignee: Albany Medical College, Albany, NY (US)

( * ) Notice: Subject to any disclaimer, the term of this patent is extended or adjusted under 35 U.S.C. 154(b) by 523 days.

(21) Appl. No.: 12/865,673

(22) PCT Filed: Feb. 2, 2009

(86) PCT No.: PCT/US2009/032815
§ 371 (c)(1),
(2), (4) Date: Dec. 28, 2010

(87) PCT Pub. No.: WO2009/134489
PCT Pub. Date: Nov. 5, 2009

(65) Prior Publication Data
US 2011/0104104 A1    May 5, 2011

Related U.S. Application Data

(60) Provisional application No. 61/025,623, filed on Feb. 1, 2008.

(51) Int. Cl.
| | | |
|---|---|---|
| *A61K 38/21* | (2006.01) | |
| *A61K 38/19* | (2006.01) | |
| *A61K 39/395* | (2006.01) | |
| *A61P 31/04* | (2006.01) | |
| *C07K 16/24* | (2006.01) | |
| *A61K 39/00* | (2006.01) | |

(52) U.S. Cl.
CPC ...... *C07K 16/249* (2013.01); *A61K 2039/505* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 5,578,707 A | 11/1996 | Novick et al. | |
| 6,830,752 B2 * | 12/2004 | Buyse et al. | 424/135.1 |
| 7,335,743 B2 * | 2/2008 | Welcher et al. | 530/388.15 |
| 7,592,326 B2 * | 9/2009 | Karaolis | 514/47 |
| 7,910,708 B2 * | 3/2011 | Campbell et al. | 530/388.23 |
| 2003/0138404 A1 | 7/2003 | Maroun | |
| 2005/0036951 A1 | 2/2005 | Henderson | |
| 2005/0234089 A1 | 10/2005 | Meisel et al. | |
| 2007/0160609 A1 | 7/2007 | Maroun | |

OTHER PUBLICATIONS

Condos et al. 1994, Chest, vol. 125, pp. 2146-2155.*
Sun et al. (2008), Nat. Med. vol. 14(5), pp. 558-564.*
Hirschtick et al. (1995), N. Engl. J. Med., vol. 333, pp. 845-851.*
Baumgarth et al. (1996), J. of Virology, vol. 70, No. 7, p. 4411-4418.*
Beadling et al. (2004), Curr. Opin. Infect Dis., vol. 17, p. 185-191.*
Ito et al. "Interlukin-10 Inhibits Expression of Both Interferon alpha- and Interferon gamma-Induced Genes by Supressing Tyrosine Phosphorylation of STAT1", Blood, 93(5):1456-1463 (1999).
Bakaletz, L. "Developing Animal Models for Polymicrobial Diseases", Nature Reviews Microbiology 2:552-568 (2004).
Kurschner et al. "Construction, Purification, and Characterization of New Interferon gamma (INFgamma) Inhibitor Proteins", The J. Biol. Chem. 267(13):9354-9360 (1992).
PCT ISA210 International Search Report for PCT/US2009/032815 (Feb. 2, 2009).

* cited by examiner

*Primary Examiner* — Christine J Saoud
*Assistant Examiner* — Jegatheesan Seharaseyon
(74) *Attorney, Agent, or Firm* — LeClairRyan, a Professional Corporation

(57) ABSTRACT

The present invention is directed to methods for treating a viral respiratory infection in a subject, preventing polymicrobial synergy in a subject, or preventing a bacterial infection in a subject. These methods include selecting a subject with a viral respiratory infection, a subject susceptible to polymicrobial synergy, or a subject susceptible to bacterial infection, respectively. In each case a therapeutic agent that inhibits interferon-gamma (IFNγ) is provided and administered to the selected subject under conditions effective to treat the viral respiratory infection, to prevent polymicrobial synergy, or to prevent a bacterial infection, respectively.

6 Claims, 16 Drawing Sheets

BLOCKAGE OF INTERFERON-GAMMA FOR PREVENTION OF POLYMICROBIAL SYNERGY

This application claims the benefit of U.S. Provisional Patent Application Ser. No. 61/025,623, filed Feb. 1, 2008, which is hereby incorporated by reference in its entirety.

This invention was made with government support under grant number RO1 AI41715 awarded by National Institute of Allergy and Infectious Diseases, National Institute of Health. The government has certain rights in this invention.

FIELD OF THE INVENTION

The present invention is directed to blockage of interferon-gamma for prevention of polymicrobial synergy.

BACKGROUND OF THE INVENTION

Influenza virus and *S. pneumoniae* are the two pathogens that cause the majority of respiratory infections in humans. Although influenza infection alone may cause pneumonia, secondary bacterial pneumonia is a major cause of excess morbidity and mortality during typical influenza pandemics, including the major pandemic of 1918-1919 (Brundage, J. F., "Interactions Between Influenza and Bacterial Respiratory Pathogens: Implications for Pandemic Preparedness," *Lancet Infect Dis* 6:303-12 (2006), Stiver, H. G., "The Threat and Prospects for Control of an Influenza Pandemic," *Expert Rev Vaccines* 3:35-42 (2004)). Indeed, cultivable pneumococci could be found in more than half of the blood samples obtained from soldiers with influenza during the 1918 pandemic, suggesting that more individuals died from secondary bacterial pneumonia than from the primary virus infection (Spooner et al., "A Bacteriologic Study of the Influenza Epidemic at Camp Devens, Mass.," *Jama* 72:155-159 (1919), Hall et al., "The Epidemic of Pneumonia Following Influenza at Camp Logan, Texas," *Jama* 71:1986-87 (1918)). The fact that secondary bacterial infections are responsible for a significant proportion of deaths during influenza pandemics has led to a recent call for stockpiling of antibiotics and pneumococcal conjugate vaccine as part of a plan for influenza preparedness (Klugman et al., "Pneumococcal Vaccines and Flu Preparedness," Science 316:49-50 (2007)).

Several factors have been proposed to be involved in this viral-bacterial synergy, including suppression of neutrophil function (Craft et al., "Effect of Virus Infections on Polymorph Function in Children," *Br Med J* 1:1570 (1976), Abramson et al., "Polymorphonuclear Leukocyte Dysfunction During Influenza Virus Infection in Chinchillas," *J Infect Dis* 143:836-45 (1981), McNamee et al., "Both Influenza-Induced Neutrophil Dysfunction and Neutrophil-Independent Mechanisms Contribute to Increased Susceptibility to a Secondary Streptococcus Pneumoniae Infection," *Infect Immun* 74: 6707-21 (2006)), increased bacterial adherence to epithelia due to upregulation of platelet-activating factor receptor expression (van der Sluijs et al., "Involvement of the Platelet-Activating Factor Receptor in Host Defense Against *Streptococcus Pneumoniae* During Postinfluenza Pneumonia," *Am J Physiol Lung Cell Mol Physiol* 290: L 194-9 (2006), (McCullers et al., "Lethal Synergism Between Influenza Virus and *Streptococcus Pneumoniae*: Characterization of a Mouse Model and the Role of Platelet-Activating Factor Receptor," *J Infect Dis* 186:341-50 (2002)), and induction of inhibitory IL-10 (van der Sluijs et al., "IL-10 is an Important Mediator of the Enhanced Susceptibility to Pneumococcal Pneumonia After Influenza Infection," J Immunol 172:7603-9 (2004), van der Sluijs et al., "Influenza-Induced Expression of Indoleamine 2,3-dioxygenase Enhances Interleukin-10 Production and Bacterial Outgrowth During Secondary Pneumococcal Pneumonia," *J Infect Dis* 193:214-22 (2006)). The fact that increased susceptibility to various bacteria can occur following influenza infection, including *S. pneumoniae, H. influenzae, and S. aureus* (Brundage, J. F., "Interactions Between Influenza and Bacterial Respiratory Pathogens: Implications for Pandemic Preparedness," *Lancet Infect Dis* 6:303-12 (2006)), suggests a general immune defect. In addition, clinical secondary bacterial infections occur at a time when the virus begins to be cleared from the lung and the patient enters the recovery stage (Brundage, J. F., "Interactions Between Influenza and Bacterial Respiratory Pathogens: Implications for Pandemic Preparedness," *Lancet Infect Dis* 6:303-12 (2006)). This raises the possibility that the immune response that is induced against viral infection leads to decreased protection against bacterial infection. In the current invention, the innate immune mechanisms in the lung that are responsible for initial removal of pneumococci and the influence of influenza infection on these protective mechanisms have been examined. It was found that IFN-γ produced by T cells in the lung after viral infection inhibits alveolar macrophage-mediated microbial clearance and, consequently, leads to enhanced susceptibility to secondary bacterial infection.

Bacterial infections often follow influenza infection and are responsible for much of the morbidity and mortality associated with influenza. The present invention shows that interferon-γ (IFN-γ) induced by the viral infection dampens the antibacterial responses of lung tissue. IFN-γ-treated alveolar macrophages have lower phagocytic capacity and, thus, are less able to clear bacteria from infected lung tissues. In vitro treatment of alveolar macrophages with IFN-γ leads to down-regulation of the scavenger receptor MARCO, which has been associated before with complement-independent pneumococcal phagocytosis. Mice lacking either IFN-γ or its receptor show enhanced survival after secondary bacterial infection upon influenza virus exposure. Notably, neutralization of IFN-γ in virus-infected wild-type mice results in lower mortality. These findings indicate therapeutic intervention strategies for enhancing innate immunity and limiting the lethality of secondary bacterial infections.

The present invention is directed to overcoming these and other deficiencies in the art.

SUMMARY OF THE INVENTION

A first aspect of the present invention relates to a method for treating a viral respiratory infection in a subject. The method includes selecting a subject with a viral respiratory infection and providing a therapeutic agent that inhibits interferon-gamma (IFNγ). The therapeutic agent is administered to the selected subject under conditions effective to treat the subject with the viral respiratory infection.

A second aspect of the present invention relates to a method of preventing polymicrobial synergy in a subject. The method includes selecting a subject susceptible to polymicrobial synergy and providing a therapeutic agent that inhibits interferon-gamma (IFNγ). The therapeutic agent is administered to the selected subject under conditions effective to prevent polymicrobial synergy in a patient.

A third aspect of the present invention relates to a method of preventing a bacterial infection in a subject. The method includes selecting a subject susceptible to bacterial infection as a result of production of interferon-gamma (IFNγ) in the subject's lungs and providing a therapeutic agent that inhibits interferon-gamma (IFNγ). The therapeutic agent is administered to the selected subject under conditions effective to prevent a bacterial infection as a result of production of interferon-gamma (IFNγ) in the subject's lungs.

Secondary bacterial infection often follows pulmonary virus infection and is a common cause of severe disease in humans, yet the mechanisms responsible for this viral-bacterial synergy in the lung are only poorly understood. The present invention reports that pulmonary IFN-γ produced during T cell responses to influenza infection in mice inhibits initial bacterial clearance from the lung by alveolar macrophages. This suppression of phagocytosis is correlated with levels of lung IFN-γ but not viral burden, and leads to enhanced susceptibility to secondary pneumococcal infection, which can be prevented by IFN-γ neutralization following influenza infection. Direct inoculation of IFN-γ can mimic influenza infection and down regulate the expression of the class A scavenger receptor MARCO (macrophage receptor with collagenous structure) on alveolar macrophages. Thus, IFN-γ, while likely facilitating induction of specific anti-influenza adaptive immunity, suppresses innate protection against extracellular bacterial pathogens in the lung.

BRIEF DESCRIPTION OF THE DRAWINGS

FIG. 1A shows that C57BL/6 mice were infected with 10 PFU of A/PR/8/34 (H1N1) influenza virus. Total weight and viral PFU in the lungs were monitored. Each point represents the mean±s.d. of four mice. FIG. 1B shows the survival of C57BL/6 mice after infection of naïve mice (−FLU) and day 7 postinfluenza infected mice (+FLU) with $10^4$ CFU of A66.1 S. pneumoniae. FIG. 1C shows relative numbers of bacteria in the lungs at 0 h (x-axis) and 4 h (y-axis) after infection of naïve C57BL/6 mice (FLU) and day 7 postinfluenza infected C57BL/6 mice (+FLU) with $10^4$ and $10^5$ CFU of A66.1 S. pneumoniae. The mean CFU±s.d. (4 mice/group) are represented as percentages of the inoculation dose. FIG. 1D shows levels of TNF-α and IL-1β in BALF 4 h after intranasal infection of naïve C57BL/6 mice (FLU) and day 7 postinfluenza infected mice (+FLU) with $10^5$ CFU of A66.1 S. pneumoniae. *** is P≤0,001 compared to naïve mice infected with only S. pneumoniae. The data are representative of at least two independent experiments.

FIG. 2A shows the correlation between pulmonary bacterial burdens at 0 h (x-axis) versus 4 h (y-axis). Each point represents the mean CFU±s.d of eight C57BL/6 mice/dose. The correlation coefficient ($r^2$) is indicated. The data shown are composite results of three independent experiments (P=0.003). FIG. 2B shows the numbers of bacteria (mean±s.d) remaining in the BALF after infection with $10^4$ CFU S. pneumoniae. PMN is mice depleted of neutrophils and +PMN is neutrophil-competent mice (45 mice/group). FIG. 2C shows relative numbers of bacteria remaining in the lungs and BALF 4 h after infection with $10^5$ CFU of S. pneumoniae. Lip are untreated mice, PBS is PBS-liposome treated mice, and Clodr is clodronate-liposome treated mice (n=5). FIG. 2D shows flow cytometry analysis of BALF cells from naïve mice (FLU) and viral-infected mice (+FLU). FIG. 2E shows levels of CD11c$^+$ cells in naïve and viral-infected mice (n=4). FIG. 2F shows BALF phagocytes after 2 h inoculation of naïve mice or viral-infected mice with labeled S. pneumoniae. The results are representative of three mice per group and mean percentages are shown. FIG. 2G shows fluorescence microscopy analysis of sorted phagocytes from the BALF of mice infected with $10^6$ CFU of S. pneumoniae. Scale bars, 50 µM. The bar graphs show the average MFI±s.d. of three microscopic fields per group. *** is P<0.001, compared to PBS-liposome treated mice (FIG. 2C) or influenza infected mice (FIGS. 2E and 2G). The data are representative of two independent experiments (FIGS. 2D-G).

FIG. 3A shows numbers of bacterial CFU, and FIG. 3B shows levels of IFN-γ in BALF at various days after influenza infection and 4 h after infection with $10^4$ CFU A66.1 S. pneumoniae (four mice/group). FIG. 3C shows numbers of bacteria in the lungs 4 h after pneumococcal infection of C57BL/6 naïve (FLU) and day 9 postinfluenza mice (+FLU). Numbers of bacteria are in (FIG. 3D) C57BL/6 BALF and (FIG. 3E) BALB/c lungs 4 h after infecting naïve and day 9 postinfluenza mice with $10^5$ CFU of S. pneumoniae D39. FIG. 3F shows survival of C57BL/6 WT and Ifngr1$^{-/-}$ mice after challenge with $10^4$ CFU of A66.1 S. pneumoniae following influenza infection (68 mice/group). FIG. 3G shows survival of C57BL/6 WT and Ifng$^{-/-}$ after challenge with $10^5$ CFU of D39 S. pneumoniae following influenza infection (68 mice/group). FIG. 3H shows the survival of BALB/c WT and Ifng$^{-/-}$ mice after challenge with $10^5$ CFU of D39 S. pneumoniae following influenza infection (68 mice/group). In FIGS. 3F-H, survival of the mice was monitored daily. Control WT and Ifng1$^{-/-}$ or Ifng$^{-/-}$ mice infected with only influenza virus or S. pneumoniae all survived. * is P<0.05,  is P<0.01, and * is P<0.001, relative to naïve (FIGS. 3A-B) or influenza infected WT mice (FIGS. 3C-E).

FIG. 4A shows flow cytometric analysis of in vitro bacterial uptake by CD11c$^+$ BALF cells incubated with IFN-γ (left) and of in vivo bacterial uptake by CD11c$^+$ BALF cells from IFN-γ-treated mice (right). FIG. 4B shows numbers of bacteria in BALF 4 h after infection of PBS-treated (PBS) and IFN-γ-treated (IFN-γ) C57BL/6 mice with $10^5$ CFU of A66.1 S. pneumoniae. FIG. 4C shows flow cytometric analysis for surface expression of MARCO on CD11c$^+$ BALF cells from C57BL/6 mice after either in vitro or in vivo treatment with IFN-γ. MHCII surface expression is also shown. FIG. 4D shows MARCO-specific antibody (ED31) mediated blocking of bacterial uptake by CD11c$^+$ BALF cells, as shown by flow cytometric analysis. Gray histograms, isotype control. The data are representative of at least two independent experiments with 35 mice per group. ** is P<0.01, compared to PBS treated mice.

FIG. 6A shows levels of bacterial CFU in BALF 4 h after intranasal inoculation of $10^5$ CFU S. pneumoniae into naïve C57BL/6 mice or mice infected 8 days earlier with 10 PFU of influenza virus. Influenza infected mice were also treated with rat IgG or XMG1.2 intranasally on day 5 after viral inoculation. FIG. 6B shows survival of C57BL/6 mice after IFN-γ neutralization and infection with $10^5$ CFU of S. pneumoniae on day 8 postinfluenza infection (6-8 mice/group). FIG. 6C shows survival of BALB/c mice after IFN-γ neutralization and infection with $10^5$ CFU S. pneumoniae on day 9 postinfluenza infection (8 mice/group). FIG. 6D shows IFN-γ levels and FIG. 6E shows bacterial CFU in the BALF of naïve and day 8 postinfluenza infected C57BL/6 WT and Il10$^{-/-}$ mice 4 h after infection with $10^5$ CFU of S. pneumoniae. FIG. 6F shows survival of C57BL/6 WT and Il10$^{-/-}$ mice after IFN-γ neutralization and infection with $10^5$ CFU S. pneumoniae on day 8 postinfluenza infection (8-13 mice/group). Control WT and Il10$^{-/-}$ mice infected with only influenza virus or S. pneumoniae all survived. FIG. 6G shows viral PFU in BALF of C57BL/6 WT and Il10$^{-/-}$ mice on day 8 after influenza infection. ** is P<0.01 compared to influenza infected WT mice.

FIG. 7A shows survival of C57BL/6 mice after respiratory infection with the indicated doses of S. pneumoniae (5 mice/group). FIGS. 7B-C depict bar graphs showing the relative numbers of bacteria in C57BL/6 wild-type lungs and BALF (FIG. 7B) scid lungs, and (FIG. 7C) Rag2$^{-/-}$ BALF 4 hr after infection with $10^5$ CFU of A66.1 S. pneumoniae (5 mice/group). FIG. 7D shows flow cytometry analysis of C57BL/6 BALF cells 4 and 24 hr after infection with $10^4$ CFU S. pneumoniae. –PMN is mice depleted of neutrophils using anti-Ly6G mAb treatment and +PMN is neutrophil-competent mice (4-5 mice/group). FIG. 7E shows relative numbers of bacteria remaining in the lungs 2 and 4 hr after infection of C57BL/6 mice with $10^5$ CFU S. pneumoniae. –PMN is mice depleted of neutrophils and +PMN is neutrophil-competent mice. In FIGS. 7B-C, and E, the mean CFU±s.d. (5 mice/group) are represented as percentages of the inoculation dose. FIG. 7F shows flow cytometry analysis of CD11c$^+$ alveolar macrophages at different time points after infection of C57BL/6 mice with $10^5$ CFU of PKH26 red fluorescent-labeled S. pneumoniae. The results are representative of three mice per group. FIG. 7G shows numbers of bacteria (mean CFU±s.d) in the lungs after infection of C57BL/6 wild-type and C3$^{-/-}$ mice with $10^5$ CFU of S. pneumoniae (4 mice/time point). The data are representative of two independent experiments, * is P<0.05, compared to wild-type mice.

FIG. 8A shows flow cytometry analysis of CD11$^+$Ly6G$^+$ neutrophils in BALF 4 hr after superinfection of C57BL/6 wild-type and Ifngr1$^{-/-}$ mice with $10^5$ CFU S. pneumoniae on day 9 of viral infection. –PMN is mice depleted of neutrophils using anti-Ly6G mAb treatment and +PMN is neutrophil-competent mice. Pooled BALF cells from three mice per group are shown. FIG. 8B shows numbers of bacteria in BALF 4 hr after pneumococcal infection of day 9 postinfluenza mice (+FLU). –PMN is neutrophil-depleted mice.  is P<0.01 and * is P<0.001, relative to influenza infected wild-type mice.

FIG. 10A shows lung lymphocytes were isolated from C57BL/6 mice on day 7 after influenza infection and intracellular IFN-γ expression was determined by flow cytometry. Results from the lung lymphocyte gate are shown. FIG. 10B shows C57BL/6 wild-type and Cd4$^{-/-}$ mice were infected with influenza virus and challenged with $10^5$ CFU of A66.1 S. pneumoniae on day 8 after viral infection.

FIG. 11A shows the mean weight change of BALB/c mice after infection with 10 PFU of influenza virus, IFN-γ neutralization, and inoculation of $10^5$ CFU S. pneumoniae D39 on day 9 postinfluenza infection (8 mice/group). Mean levels±s.d of viral PFU (FIG. 11B); TNF-α (FIG. 11C); and IL-1β in BALF (FIG. 11D) 4 hr after intranasal inoculation of $10^5$ CFU S. pneumoniae into either naïve C57BL/6 mice or mice infected 8 days earlier with 10 PFU of influenza virus (5-7 mice/group). Influenza infected mice were also treated with rat IgG or XMG1.2 anti-IFN-γ mAb intranasally on day 5 after viral inoculation. The data are representative of two independent experiments.  is P<0.01 and * is P<0.001, compared to influenza infected wild-type mice.

FIG. 13A shows levels of RNA from CD11c+ alveolar macrophages obtained from day 8 post-influenza (10 PFU A/PR/8) infected wild-type (WT) and IFN-g–/– mice, relative to naïve, uninfected mice (NM). FIG. 13B shows levels of RNA from CD11c+ alveolar macrophages obtained from day 8 post-influenza (10 PFU A/PR/8) infected wild-type (WT) treated with normal rat Ig or rat anti-IFN-γ antibody (XMG1.2). In both FIG. 13A and FIG. 13B, expression of both MR and MARCO were decreased in influenza-infected mice (RNA levels <100%) and this suppression was relieved in the absence of IFN-γ.

DETAILED DESCRIPTION OF THE INVENTION

Figure 1:
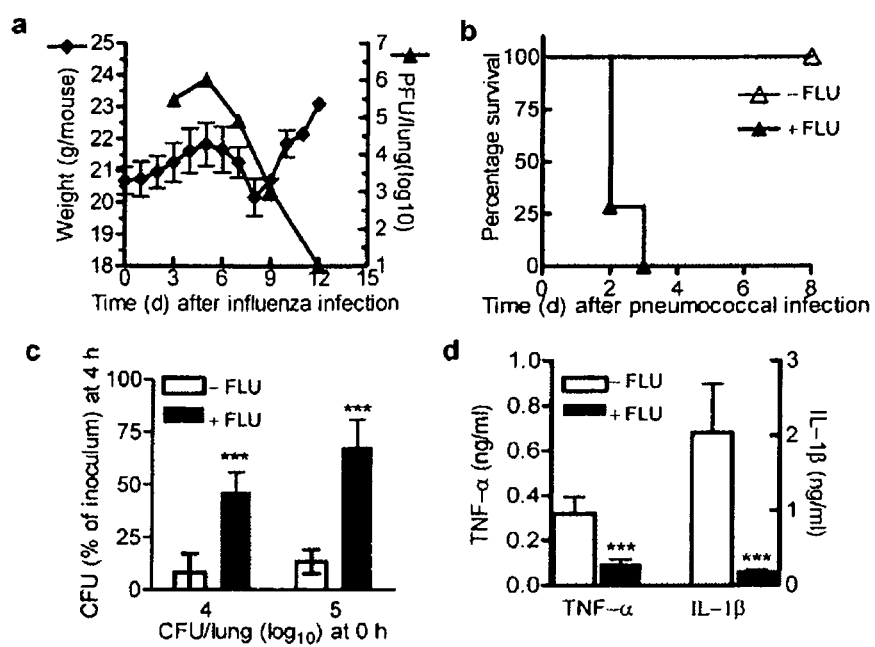
FIGS. 1A-D show that influenza infection inhibits initial resistance of mice to pneumococcal infection.

A first aspect of the present invention relates to a method for treating a viral respiratory infection in a subject. The method includes selecting a subject with a viral respiratory infection and providing a therapeutic agent that inhibits interferon-gamma (IFNγ). The therapeutic agent is administered to the selected subject under conditions effective to treat the subject with the viral respiratory infection.

For each method described herein, a subject in need may be selected. The methods may be carried out in a human subject.

Organisms which could cause infection to be treated include *Streptococcus pneumoniae. Streptococcus pyogenes, Haemophilus influenzae, Staphylococcus aureus, Neisseria meningitidis, Mycobacterium tuberculosis, Bordetella pertussis*, and, in immunocompromised patients, *Pseudomonas aeruginosa*. These are described in van der Sluijs et al, "Involvement of the Platelet-Activating Factor Receptor in Host Defense Against *Streptococcus Pneumoniae* During Postinfluenza Pneumonia," *Am J Physiol Lung Cell Mol Physiol* 290:L194-9 (2006), McCullers et al., "Role of Neuraminidase in Lethal Synergism Between Influenza Virus and *Streptococcus Pneumoniae*," *J Infect Dis* 187: 1000-9 (2003), Ziaie et al, "Isolation of Bacteria Causing Secondary Bacterial Infection in the Lesions of Cutaneous Leishmaniasis," *Ind J Dermatology* 53(3) 129-131 (2008), and Smith et al., "Cooperation Between Viral and Bacterial Pathogens in Causing Human Respiratory Disease," in Polymicrobial Diseases, Eds. Brogden and Guthmiller, *ASM Press*, Herndon, Va., 2002, which are hereby incorporated by reference in their entirety.

The therapeutic agent of the present invention may be selected from the group consisting of an anti-IFNγ antibody or a fragment thereof that binds to the IFNγ receptor, a soluble IFNγ receptor, a hybrid IFNγ receptor molecule, and an anti-IFNγ receptor antibody.

Interferon-γ (IFN-γ) is produced by lymphocytes (CD4+, CD8+, NK cells) as well as macrophages and perhaps neutrophils. It is induced by a number of signals, including interleukin-12 (hereafter, IL-12) and, similarly, IL-18 and, in turn. induces hundreds of genes, including its own inducers. Exposure to various pathogens can stimulate at least two patterns of cytokine production by CD4+ T cells. Th1 cells are defined by production of IFN-γ, lymphotoxin and IL-2. Th2 cells are defined by production of IL-4, IL-5, IL-9, IL-10, and IL-13. The antimicrobial activity induced by IFN-γ encompasses intracellular and extracellular parasites, bacteria, fungi and viruses.

nucleic acid and amino acid sequences for IFNγ may be found using the following reference sequence ID numbers on GenBank: IFNγ from mouse (NM_008337.3) and IFNγ from human (NM_000619).

Various methods of producing antibodies with a known antigen are well-known to those ordinarily skilled in the art (*Antibodies; A Laboratory Manual* (Harlow & Lane eds., 1988), which is hereby incorporated by reference in its entirety). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In particular, monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler et al., "Continuous Cultures of Fused Cells Secreting Antibody of Predefined Specificity," *Nature*, 256:495-97 (1975), which is hereby incorporated by reference in its entirety.

Procedures for raising polyclonal antibodies are also well known. Typically, such antibodies can be raised by administering the protein or polypeptide of interest subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in ANTIBODIES: A LABORATORY MANUAL (Harlow & Lane eds., 1988), which is hereby incorporated by reference in its entirety.

In addition to utilizing whole antibodies, the processes of the present invention encompass use of binding portions of such antibodies. Such binding portions include fragments. Domain antibodies (dAbs) (see, e.g., Holt et al., "Domain Antibodies: Proteins for Therapy," *Trends in Biotechnology* 21:484-490 (2003), which is hereby incorporated by reference in its entirety) are also suitable for the methods of the present invention. These antibody fragments can be made by conventional procedures, such as proteolytic fragmentation procedures, as described in J. Goding, *Monoclonal Antibodies: Principles and Practice* 98-118 (1983), which is hereby incorporated by reference in its entirety.

The interferon-gamma receptor (IFNGR) is a receptor which binds IFN-γ, the sole member of interferon type II. The human interferon-gamma receptor complex consists the heterodimer of two chains: IFNGR1 and IFNGR2 (Bach et al., "The IFN Gamma Receptor: A Paradigm for Cytokine Receptor Signaling," *Annu Rev Immunol* 15: 563-91 (1997), Pestka et al., "The Interferon Gamma (IFN-Gamma) Receptor: A Paradigm for the Multichain Cytokine Receptor," *Cytokine Growth Factor Rev* 8 (3): 189-206 (1997), which are hereby incorporated by reference in its entirety). In unstimulated cells, these subunits are not preassociated with each other but rather associate through their intracellular domains with inactive forms of specific Janus family kinases (Jak1 and Jak2). Jak1 and Jak2 constitutively associate with IFNGR1 and IFNGR2, respectively. Binding of IFN-γ to IFNGR1 induces the rapid dimerization of IFNGR1 chains, thereby forming a site that is recognized by the extracellular domain of IFNGR2. The ligand-induced assembly of the complete receptor complex contains two IFNGR1 and two IFNGR2 subunits which bring into close juxtaposition the intracellular domains of these proteins together with the inactive Jak1 and Jak2 kinases that they associate with. In this complex, Jak1 and Jak2 transactivate one another and then phosphorylate IFNGR1, thereby forming a paired set of Stat1 docking sites on the ligated receptor. Two Stat1 molecules then associate with the paired docking sites, are brought into close proximity with receptor-associated activated JAK kinases, and are activated by phosphorylation of the Stat1. Tyrosine-phosphorylated Stat1 molecules dissociate from their receptor tether and form homodimeric complexes. Activated Stat1 translocates to the nucleus and, after binding to a specific sequence in the promoter region of immediate-early IFN-γ-inducible genes, effects gene transcription.

Exemplary therapeutic agents for inhibiting IFNγ activity include heparin and IL-10. These are described in Hatakeyama et al., "Heparin Inhibits IFN-Gamma-Induced Fractalkine/CX3CL1 Expression in Human Endothelial Cells," *Inflammation* 28(1):7-13 (2004) and Song et al., "Interleukin-10 Inhibits Interferon-Gamma-Induced Intercellular Adhesion Molecule-1 Gene Transcription in Human Monocytes," *Blood* 89(12):4461-9 (1997), which are hereby incorporated by reference in their entirety). Further, IL-4, IL-13, and TGF-beta can alter immune networks and, ultimately, decrease IFN-gamma expression. Glucocorticoids and prostaglandins also inhibit IFN-gamma production.

The therapeutic of the present invention may be administered in combination with an antiviral or antibacterial therapy.

The term "antiviral therapy" is meant to include the use of antiviral drugs, are a class of medication used specifically for treating viral infections. Similar to antibiotics for bacteria, specific antivirals are used for specific viruses. Antiviral drugs are one class of antimicrobials, a larger group which also includes antibiotic, antifungal and antiparasitic drugs. They are relatively harmless to the host, and therefore can be used to treat infections. They should be distinguished from viricides, which actively destroy virus particles outside the body. It is important to note that almost all antimicrobials, including anti-virals, are subject to drug resistance as the pathogens evolve to survive exposure to the treatment.

The term "antibacterial therapy" is meant to include use of anything that destroys bacteria or suppresses their growth or their ability to reproduce. Antibiotic drugs all have antibacterial properties. Antibacterial drugs are derived from bacteria or molds or from de novo synthesis. "Antibiotic," which is often used synonymously with "antibacterial drug," technically refers only to antimicrobials derived from bacteria or molds. Antibacterials have many mechanisms of action, including inhibiting cell wall synthesis, activating enzymes that destroy the cell wall, increasing cell membrane permeability, and interfering with protein synthesis and nucleic acid metabolism. Examples of antibacterial drugs include: warfarin, theophylline, phenytoin, and digoxin. See Rice et al., "Antibacterial Prescribing and Warfarin: A Review," *Br Dental J* 194:411-415 (2003), which is hereby incorporated by reference in its entirety.

The therapeutic of the present invention may be administered to a subject, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The therapeutic of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The therapeutic of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the therapeutic may be incorporated with excipients and used in the form of tablets, capsules, elixirs, suspensions, syrups, and the like. Various other materials may be present as coatings or to modify the physical form of the dosage unit.

The therapeutic may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The therapeutic of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form, such as in a nebulizer or atomizer.

The therapeutic of this invention may be administered in sufficient amounts to inhibit interferon-gamma (IFNγ) to provide a therapeutic benefit without undue adverse effects or with medically acceptable physiological effects which can be determined by those skilled in the medical arts.

Dosages of the therapeutic will depend primarily on factors, such as the condition being treated, the age, weight, and health of the patient, and may thus vary among patients. The dosage will be adjusted to balance the therapeutic benefit against any viral toxicity or side effects.

A second aspect of the present invention relates to a method of preventing polymicrobial synergy in a subject. The method includes selecting a subject susceptible to polymicrobial synergy and providing a therapeutic agent that inhibits interferon-gamma (IFNγ). The therapeutic agent is administered to the selected subject under conditions effective to prevent polymicrobial synergy in a patient.

The term "synergy" is meant to include the cooperative interaction of two or more bacterial species that produces a result not achieved by the individual bacterium acting alone. The pathogenic bacteria present in polymicrobial infections exhibit synergistic effects in their ability to cause infections. Synergy is described in Mastropaolo et al., "Synergy in Polymicrobial Infections in a Mouse Model of Type 2 Diabetes," *Inf Imm* 73(9):6055-6063 (2005), Brook, I., "Synergistic Aerobic and Anaerobic Infections," *Clin Ther* 10 Suppl A: 19-35 (1987), which are hereby incorporated by reference in their entirety. Further, based on clinical and experimental results with animal models, it has been hypothesized that different types of bacteria promote synergy within polymicrobial infections via different mechanisms (Rotstein et al., "Mechanisms of Microbial Synergy in Polymicrobial Surgical Infections," *Rev Infect Dis* 7:151-170 (1985), which is hereby incorporated by reference in its entirety).

Bowler et al., "Wound Microbiology and Associated Approaches to Wound Management," *Clin Microb Rev* 14(2):244-269 (2001), which is hereby incorporated by reference in its entirety, reports that microbial synergy may increase the net pathogenic effect and, therefore, the severity of infection in several ways: (i) oxygen consumption by aerobic bacteria induces tissue hypoxia and a lowering of the redox potential, which favors the growth of anaerobic bacteria; (ii) specific nutrients produced by one bacterium may encourage the growth of fastidious and potentially pathogenic cohabiting microorganisms; and (iii) some anaerobes are able to impair host immune cell function and thus provide a competitive advantage to themselves and other, cohabiting microorganisms.

Kingston et al., "Current Hypotheses on Synergistic Microbial Gangrene," *Br J Surg* 77(3):260-4 (1990), which is hereby incorporated by reference in its entirety, argued that all species associated with a microbial disease should be considered potentially synergistic, rather than a single species being causative, as is commonly perceived.

This aspect of the present invention can be carried out by formulating and administering the therapeutic agent that inhibits interferon-gamma (IFNγ) in substantially the same manner as described above.

A third aspect of the present invention relates to a method of preventing a bacterial infection in a subject. The method includes selecting a subject susceptible to bacterial infection as a result of production of interferon-gamma (IFNγ) in the subject's lungs and providing a therapeutic agent that inhibits interferon-gamma (IFNγ). The therapeutic agent is administered to the selected subject under conditions effective to prevent a bacterial infection as a result of production of interferon-gamma (IFNγ) in the subject's lungs.

The bacterial infection may be associated with a viral infection, particularly a respiratory viral infection.

The bacterial infection may be caused by *S. pneumoniae, H. influenzae, S. aureu, M. catarrhalis, P, carinii*, or *P. aeriuginosa*.

This aspect of the present invention can be carried out by formulating and administering the therapeutic agent that inhibits interferon-gamma (IFNγ) in substantially the same manner as described above.

The term "Viral respiratory infections" is meant to include common respiratory infections (e.g. colds) in both adults and children. Most of these infections are fairly mild, self-limiting and confined to the upper respiratory tract (URT). Most are probably viral induced—at least initially. However, in infants and children, URT infections may spread downwards and cause more severe infections and even death.

In additions to colds, URT viral respiratory infections may include pharyngitis (sore throat), tonsillitis, sinusitis and otitis media (painful inflammatory conditions of sinuses and middle ear), and influenza.

Viral respiratory infections confined to the lower respiratory tract (LRT) include laryngo-tracheo bronchitis (croup), acute bronchitis, acute bronchiolitis, and pneumonia and bronchopneumonia.

Production of IFNγ in the subject's lungs may result from viral infection, chronic obstructive pulmonary disease, asthma, or cystic fibrosis, in addition to viral infection.

EXAMPLES

The following examples are provided to illustrate embodiments of the present invention but are by no means intended to limit its scope.

Materials and Methods for Examples 1-4

Mouse Model of Viral and Bacterial Infection 6-8 week old C57BL/6 and BALB/c WT mice were purchased from Taconic Laboratories and Charles River. C57BL/6 $Rag2^{-/-}$ mice were purchased from Taconic Laboratories. C57BL/6 scid, $Ifng^{-/-}$, $Ifngr1^{-/-}$, $Cd4^{-/-}$, $Cd8a^{-/-}$, $C3^{-/-}$, and $Il10^{-/-}$ mice, and BALB/c $Ifng^{-/-}$ were purchased from the Jackson Laboratory. All animal experiments were performed at Albany Medical College following IACUC guidelines.

Viral challenge was performed by intranasally ("i.n.") inoculation of 10 PFU of A/PR8/34 influenza virus (Charles River Laboratories) to anesthetized mice in 50 μl PBS. Anesthetized mice were inoculated i.n. with *S. pneumoniae* in 50 μl of Ringer's solution to induce bacterial pneumonia. Studies examining superinfection with pneumococci were performed at the time that the mice began to regain weight following primary viral infection.

Titers of virus stocks and viral levels in the BALF and lungs of infected mice were determined by plaque assays on MDCK cell monolayers. Respiratory bacterial burdens were measured by sacrificing infected mice at various time points as indicated, and incubating serial 10-fold dilutions of BALF and lung homogenates on blood agar plates at 37° C. overnight. Studies examining superinfection with pneumococci were all performed at the time that the mice began to regain weight following primary viral infection, which varied among individual experiments from days 7 to 10 after sublethal influenza infection. An infection dose of $10^5$ CFU was chosen for bacterial clearance studies and a dose of $10^4$ CFU was chosen for survival studies in superinfected mice when the A66.1 pneumococcus strain was used.

Neutrophil Depletion

C57BL/6 mice were injected i.p. with 0.1 mg of RB6-8C5 anti-Ly6G mAb with rat IgG as a control at 48 h and 24 h before bacterial infection.

For viral infected mice, RB6-8C5 anti-Ly6G mAb was given on day 7 and day 8 after influenza infection. The efficiency of neutrophil depletion in BALF of pneumococcal-infected mice was confirmed by using Diff-Quick stained cytospin preparations and by flow cytometry (FIGS. 7D and 8A).

Alveolar Macrophage Depletion

Mouse alveolar macrophage was depleted by intranasal instillation of 100 µl of clodronate-containing liposomes (clodronate was a gift of Roche Diagnostics GmbH) 48 h before infection (Dockrell et al., "Alveolar Macrophage Apoptosis Contributes to Pneumococcal Clearance in a Resolving Model of Pulmonary Infection," *J Immunol* 171: 5380-8 (2003), which is hereby incorporated by reference in its entirety). Microscopic examination of BALF indicated >95% depletion at the time of infection.

BALF Cell Analysis

BALF was collected by washing the lung twice with 0.8 ml PBS, pH 7.2. The BALF cells were fixed with 2% paraformaldehyde, incubated with 2.4G2 mAb, and stained with APC-conjugated antibody to CD11c (Caltag Laboratories), APC-Cy7-conjugated antibody to CD11b (BD Biosciences) and PE-conjugated antibody to MHCII (eBioscience). ED31 mAb (Cell Sciences) was used in the absence of 2.4G2 mAb to analyze MARCO. Secondary PE-conjugated antibody to rat IgG was then applied. The stained cells were analyzed on a BD FACSCanto using BD FACSDiva and FlowJo software.

Binding of Pneumococci by BALF Cells

Pneumococci were labeled with a PKH26 Red Fluorescent General Cell Linker Kit (Sigma). For in vitro culture, $2.5 \times 10^5$ BALF cells (<90% macrophages as judged by differential staining) were added to a 96-well Ultra Low Attachment plate (Costar) in the presence of 10 ng/ml of IFN-γ for 4 h and then transferred to a 24-well plate at 37° C. After overnight incubation, the wells were washed with antibiotic-free RPMI medium containing 10% FBS and PKFI26-labeled pneumococci were then added at a bacteria:macrophage ratio of 3:1 and incubated for 60 min. ED31 mAb was used to block MARCO mediated bacterial uptake (van der Laan et al., "Regulation and Functional Involvement of Macrophage Scavenger Receptor MARCO in Clearance of Bacteria In Vivo" *J Immunol* 162:939-47 (1999), which is hereby incorporated by reference in its entirety) with rat IgG1 (BD Pharmingen) as an isotype control.

Figure 8:
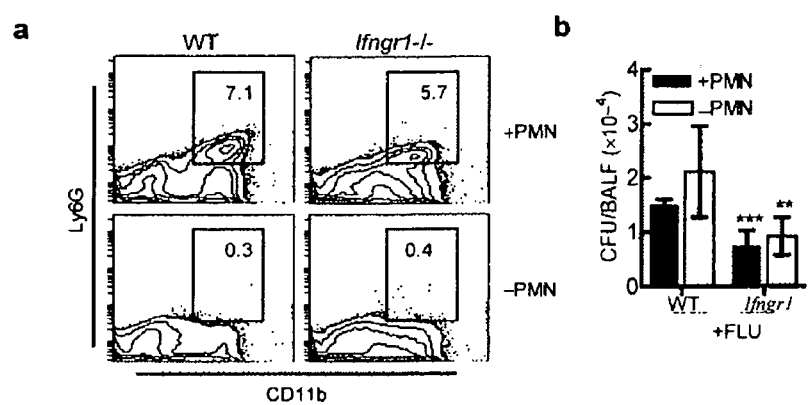
FIGS. 8A-B show neutrophil depletion in influenza infected mice.

In regards to FIG. 8, *S. pneumoniae* were labeled with a PKH26 Red Fluorescent General Cell Linker Kit (Sigma). $10^7$ CFU of *S. pneumoniae* were incubated with 2 µM PKH26 at 25° C. for 5 min, followed by addition of 1% BSA in PBS, and additional incubation for 1 min. The bacterial cell suspension was washed twice with PBS containing 1% BSA and once with PBS, and then resuspended in PBS to a concentration of $2 \times 10^6$ CFU/ml. Anesthetized mice were inoculated intranasally with 50 µl of the labeled *S. pneumoniae*. BALF cells were collected at the indicated time points and stained for CD11b and CD11c surface markers.

In Vivo Labeling of Resident Alveolar Macrophages

Anesthetized mice were inoculated intranasally with 100 µl of 10 µM PKFI26-PLC (Sigma) 5 days before influenza infection. BALF cells were collected on day 9 after influenza infection. PKH26-PLC is a phagocyte-specific, lipophilic dye that stably integrates into cell membranes for more than 21 days in vivo and is ideal for long-term staining of resting cells such as alveolar macrophages.

Immunofluorescence

Mice were infected with strain A66.1 *S. pneumoniae* seven days after influenza infection and 4 h later, BALF cells were collected and sorted on a BD FACSAria flow cytometer based upon forward and side scatter. Cytospins of the sorted phagocytes were prepared, fixed, incubated with rabbit anti-pneumococcal polysaccharide serotype 3 antiserum (Statens Serum Institute), washed, and then incubated with Texas red-conjugated anti-rabbit IgG (Jackson ImmunoResearch Laboratories, Inc.). The slides were counterstained with DAPI to visualize nuclei. Mean Fluorescence Intensity (MFI) of the stained slides was calculated by using ImageJ software.

Determination of Cytokine Production by ELISA

BALF was assayed for IFN-γ and IL-1β by ELISA using commercially available kits from R&D Systems and determined TNF-α levels using a sandwich ELISA developed in the laboratory.

IFN-γ Treatment

Mice were intranasally treated under light isoflurane anesthesia with 2 µg of recombinant mouse IFN-γ (Sigma) in 25 µl of PBS containing 1% normal mouse serum as vehicle on days −3 and −2 before bacterial infection. Control mice were treated with vehicle only.

CD4 T Cell Depletion

C57BL/6 $Cd8a^{-/-}$ mice were injected i.p. with 500 µg of GK1.5 mAb daily for three days before influenza infection, followed by inoculation every three days after infection. The efficiency of pulmonary $CD4^+$ cell depletion was confirmed by flow cytometric analysis.

In Vivo IFN-γ Neutralization

C57BL/6 and BALB/c WT mice were inoculated intraperitoneally with 600 µg of XMG1.2 mAb on days 4, 5, 6 and 7 following influenza infection, or intranasally with 80 µg of XMG1.2 mAb on day 5 after influenza infection. Other groups of mice with rat IgG were used as controls. The efficacy of IFN-γ neutralization was confirmed by ELISA on BALF samples. These studies were performed with the D39 pneumococcus strain.

Intracellular Cytokine Staining

Single-cell suspensions were obtained from lungs by collagenase D and DNase I digestion, passage through a cell strainer (BD Falcon, Bedford, Mass.), filtering through a nylon/cotton wool column and then density gradient centrifugation on Lympholyte M (Cedarlane Laboratories Limited, Ontario, Canada). The lung lymphocytes were cultured in DMEM medium containing 10% FBS for 4 hr at 37° C. in the presence of 50 ng/ml PMA, 500 ng/ml ionomycin, and 10 µg/ml Brefeldin A. The ceils were then fixed with 2% paraformaldehyde and stained with Alexa Fluor-conjugated anti-IFN-γ (BD Biosciences), FITC-conjugated anti-CD4 (BD Biosciences) and PE-conjugated anti-CD8 mAb (Caltag). The stained cells were stored in the dark at 4° C. and analyzed within 24 hr on a FACSCanto using FACSDiva software.

Statistical Analysis

The data was expressed as the mean±s.d. The students t test (to compare two samples) or ANOVA (to compare multiple samples) (GraphPad InStat 3) was used for statistical analysis. The Kaplan-Meier log rank test was performed for survival analyses. All P values >0.05 were considered not to be significant.

Example 1

Influenza Infection Impairs Innate Resistance to Pneumococci

To examine the influence of influenza infection upon subsequent susceptibility to pneumococcal infection, C57BL/6 mice were infected intranasally (i.n.) with mouse-adapted influenza virus strain, A/PR8/34 (H1N1). Within the first week of infection, viral PFU increased to nearly $10^6$/lung and the mice lost approximately 10% of their weight (FIG. 1A). Decreases in pulmonary viral PFU and weight regain commenced thereafter, indicating immune-mediated viral clearance, with levels of virus being undetectable by day 12. However, the animals showed a high susceptibility to pneumococcal infection during this recovery stage of viral infection (FIG. 1B).

It has been observed that an exaggerated inflammatory response occurs during secondary pneumococcal infection, a result that has been interpreted as a potential cause for increased susceptibility (McNamee et al., "Both Influenza-Induced Neutrophil Dysfunction and Neutrophil-Independent Mechanisms Contribute to Increased Susceptibility to a Secondary *Streptococcus pneumoniae* Infection," *Infect Immun* 74:6707-21 (2006), LeVine et al, "Decreased Pulmonary Clearance of *S. pneumoniae* Following Influenza A Infection in Mice," *J Virol Methods* 94:173-86 (2001), which are hereby incorporated by reference in their entirety). Since these intense inflammatory responses occur at later stages of bacterial infection (24 h or later), they may result from the pathogenic effect of heightened bacterial outgrowth rather than directly from the preceding influenza infection. To avoid this conundrum, the present study focused on examining immediate pulmonary responses following pneumococcus inoculation. It was found that influenza-infected mice were defective in clearing bacteria from their lungs within 4 h after pneumococcal infection (FIG. 1C). There was no detectable leakage of bacteria into the bloodstream. Local production of tumor necrosis factor-α (TNF-α) and IL-1β was suppressed in these mice (FIG. 1D). Overall, the results indicate that influenza infection disrupts the immune response that involves initial recognition and killing of pulmonary bacteria.

Example 2

Decreased Bacterial Clearance by Alveolar Macrophages

Figure 2:
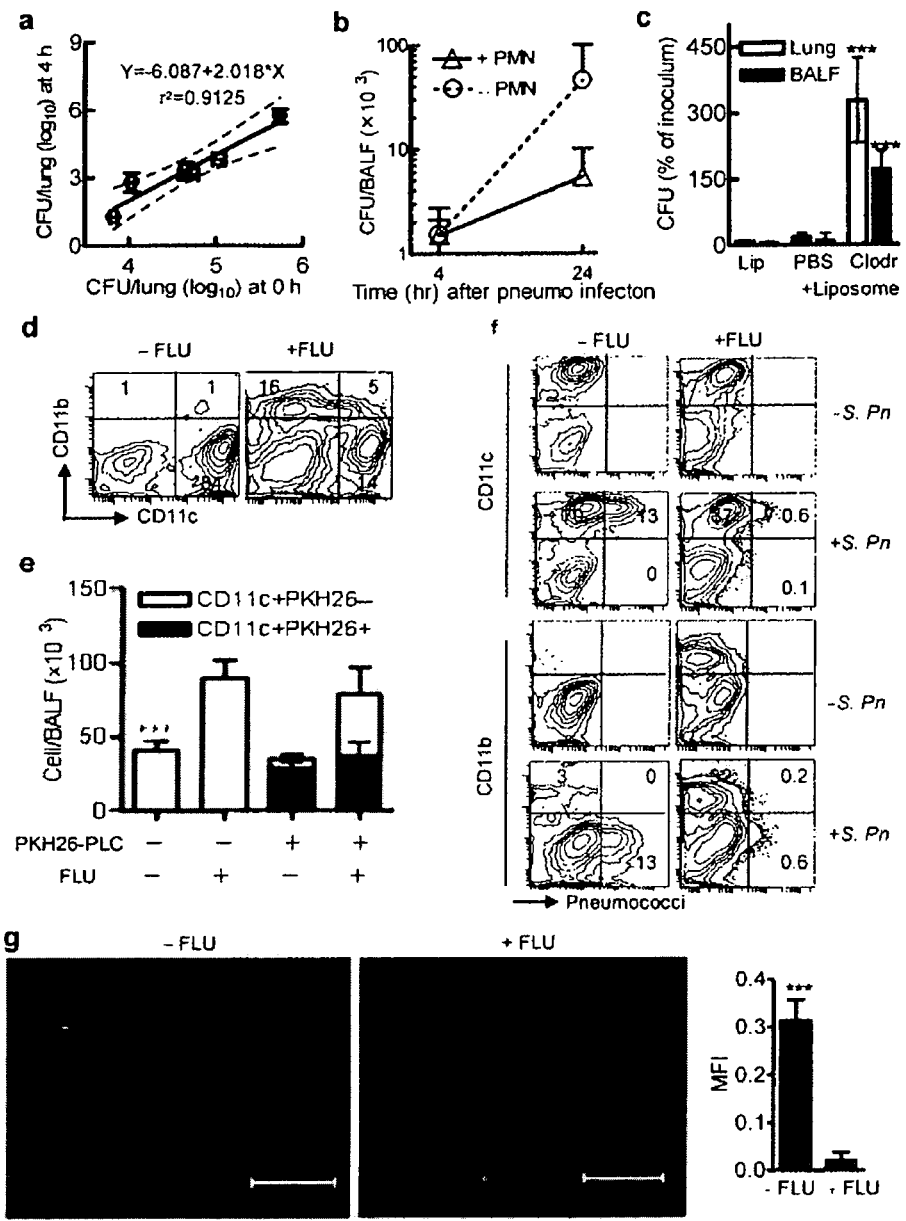
FIGS. 2A-G show that influenza infection impairs alveolar macrophage-mediated bacterial uptake.
Figure 7:
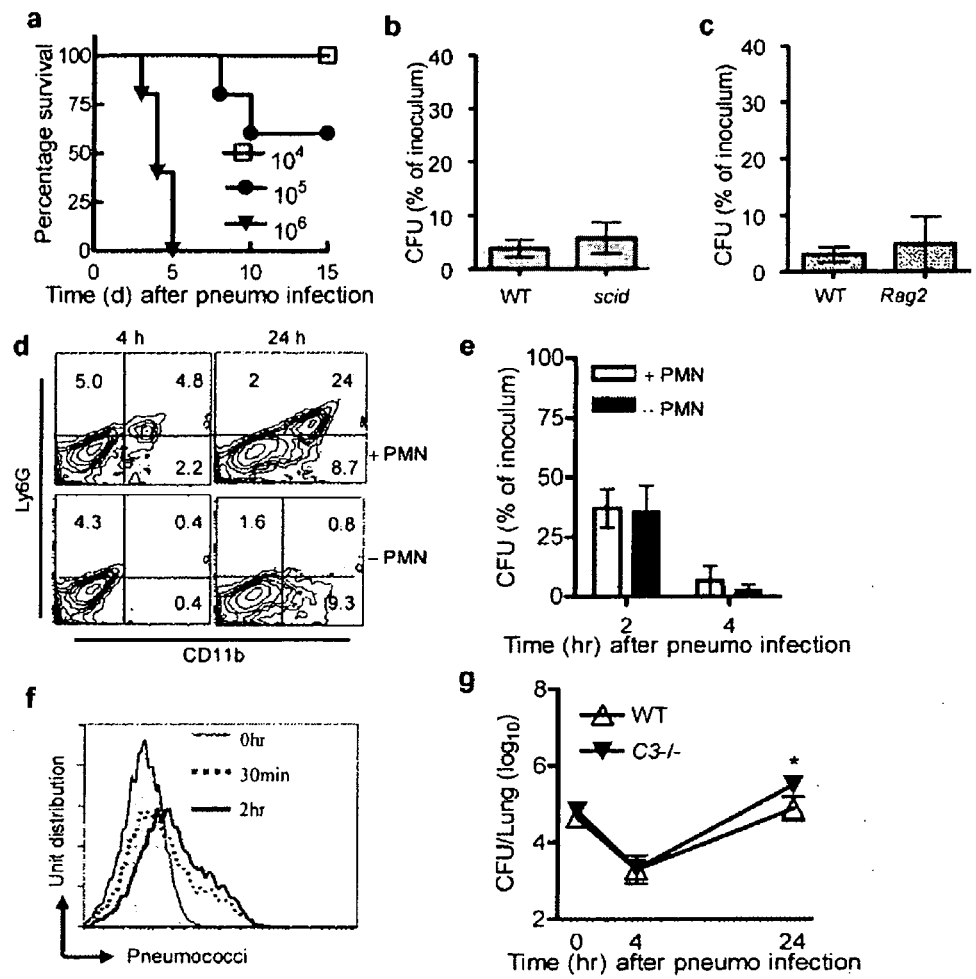
FIGS. 7A-G show bacterial clearance in naïve mice.

The normal respiratory lumen contains predominantly alveolar macrophages, which have been reported to play a key role in clearance of bacteria during subclinical infection (Dockrell et al., "Alveolar Macrophage Apoptosis Contributes to Pneumococcal Clearance in a Resolving Model of Pulmonary Infection," *J Immunol* 171:5380-8 (2003), which is hereby incorporated by reference in its entirety). The analysis showed that at an infectious dose of $10^4$-$10^5$ CFU, >90% of pneumococci were cleared within 4 h of inoculation, while at higher doses, local phagocytic capacity became overwhelmed and relative bacterial clearance was decreased (FIG. 2A). These challenge doses directly correlated with the mean survival times and bacterial lethality in nonviral-infected mice (FIG. 7).

The possible immune factors responsible for initial bacterial clearance were next examined. Initial bacterial clearance required only innate immunity which was equally efficient in naïve wild-type (WT), scid and Rag2$^{-/-}$ mice (FIG. 7B-C). Few neutrophils were observed within 4 h after pneumococcal infection and neutrophil depletion by Ly6G-specific antibody treatment did not affect initial bacterial clearance from either bronchoalveolar lavage fluid (BALF) (FIG. 8B, FIG. 7D) or lung tissue (FIG. 7E) but did influence clearance at 24 h (FIG. 8B). Bacteria were quickly bound by resident alveolar macrophages expressing CD11c (Cleret et al., "Resident CD11c+ Lung Cells are Impaired by Anthrax Toxins After Spore Infection," *J Infect Dis* 194:86-94 (2006), which is hereby incorporated by reference in its entirety) (FIG. 7F), and depletion of alveolar macrophages using liposomal clodronate (Dockrell et al., "Alveolar Macrophage Apoptosis Contributes to Pneumococcal Clearance in a Resolving Model of Pulmonary infection," *J Immunol* 171:5380-8 (2003), which is hereby incorporated by reference in its entirety), led to subsequent bacterial outgrowth in both lung tissues and alveoli (FIG. 2C). It is concluded that alveolar macrophages play an essential role in initial bacterial killing within the respiratory tract. Bacterial clearance 4 h after infection was equivalent between WT and C3-deficient mice (FIG. 7G), indicating that the pneumococci were taken up through a complement-independent mechanism, at least at this early stage of infection.

Next, it was determined whether influenza infection influences levels of macrophages in the respiratory tract. Following 4 h pneumococcal infection of naïve mice, approximately 85% of all BALF cells were CD11c$^+$ alveolar macrophages, which decreased to about 20% in viral infected mice due to increased CD11b$^+$ and CD11c$^-$CD11b$^-$ mononuclear cells (FIG. 2D). To determine the composition of the CD11c$^+$ population in viral infected mice, phagocytes in the respiratory tract of mice were labeled with PKH26-PLC dye before influenza infection. Surprisingly, the numbers of CD11c$^+$PKH26$^+$ cells after viral infection were found to be similar to those found in noninfected mice (FIG. 2E). These results indicate that influenza infection does not result in significant depletion of the CD11c$^+$ resident macrophages.

BALF cells were isolated to examine phagocytic activity. Both the CD11c$^+$ and the newly arrived CD11b$^+$ populations in influenza-infected mice were found by flow cytometry to be less efficient in mediating phagocytosis of *S. pneumoniae* (FIG. 2F). Similarly, using fluorescent microscopy to directly visualize internalized pneumococci, it was found that significantly higher numbers of bacteria were associated with phagocytes from naïve mice compared to those from influenza-infected mice (FIG. 2G). These results confirm the finding that influenza infection severely impairs alveolar macrophage mediated clearance of bacteria.

Example 3

IFN-γ Inhibits Bacterial Clearance by Alveolar Macrophages

Figure 3:
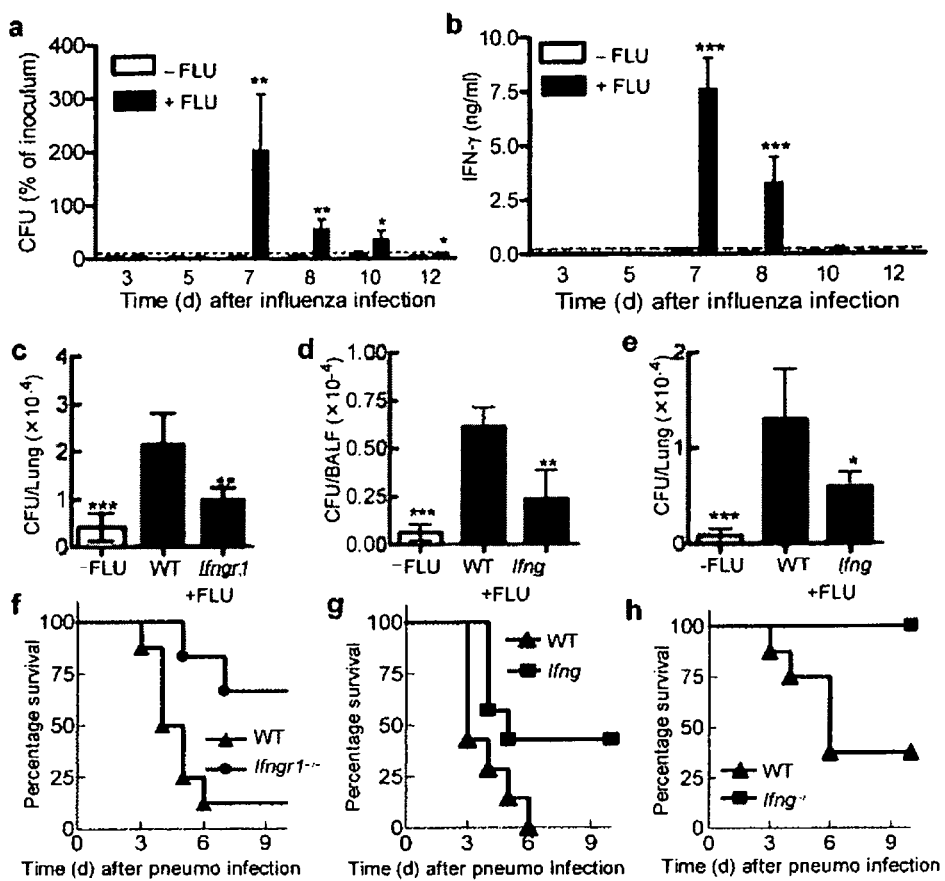
FIGS. 3A-H show the IFN-γ expressed following influenza virus infection inhibits initial bacterial clearance in the lung.

To determine the mechanism(s) responsible for inhibition of bacterial uptake by alveolar macrophages, the kinetics of bacterial clearance was measured and compared to BALF cytokine levels at various times following influenza infection. After day five, during the recovery stage of viral infection, the animals showed a decreased ability to clear bacteria from their lungs (FIG. 3A). Local expression of IFN-γ (FIG. 3B) corresponded precisely with influenza-mediated inhibition of bacterial clearance. In addition, Ifngr1$^{-/-}$ and Ifng$^{-/-}$ mice showed significant bacterial clearance following influenza infection compared to WT mice (FIG. 3C) and initial bacterial clearance in Ifngr1$^{-/-}$ mice appeared to be mediated primarily by macrophages, similar to that seen in naïve mice, since neutrophil depletion did not influence 4 h bacterial clearance (FIG. 8). As expected (La Gruta et al., "A Question of Self-Preservation; Immunopathology in Influenza Virus Infection," *Immunol Cell Biol* 85:85-92 (2007), Brown et al, "CD4 T Cell-Mediated Protection From Lethal Influenza: Perforin and Antibody-Mediated Mechanisms Give a One-Two Punch, *J Immunol* 177:2888-98 (2006), which are hereby incorporated by reference in their entirety), Ifngr1$^{-/-}$ mice did not show altered susceptibility to influenza infection and by day 12 after influenza infection, both WT and Ifngr1$^{-/-}$ mice had completely cleared the virus. However, Ifngr1$^{-/-}$ mice showed increased resistance to secondary pneumococcal infection (FIG. 3F). To confirm that these results were not strain-specific, similar studies were performed with a less virulent and commonly used pneumococcal strain, D39 (McCullers et al., "Lethal Synergism Between Influenza Virus and *Streptococcus Pneumoniae*: Characterization of a Mouse Model and the Role of Platelet-Activating Factor Receptor," *J Infect Dis* 186:341-50 (2002), which is hereby incorporated by reference in its entirety). In addition, both BALB/c and C57BL/6 mice were tested. In all cases, susceptibility to secondary pneumococcal infection was significantly attenuated in the absence of IFN-γ (FIGS. 3D-E and FIGS. 3G-H).

Figure 4:
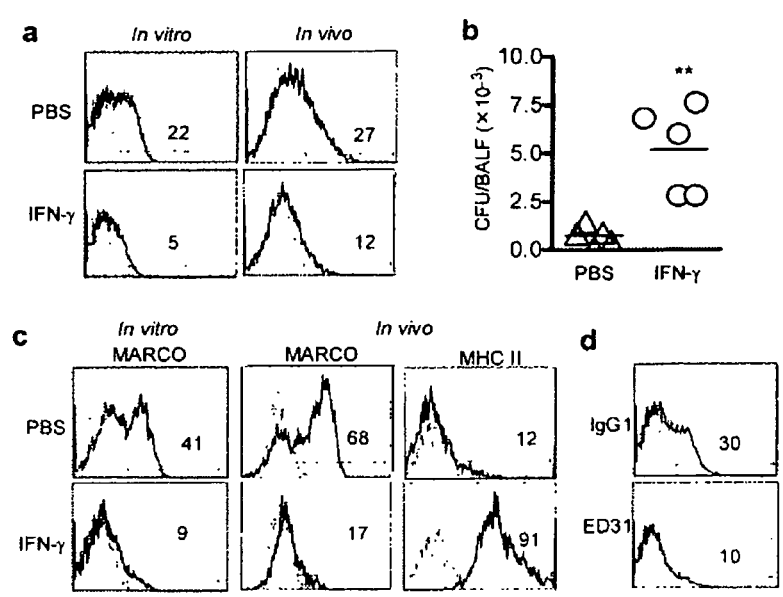
FIGS. 4A-D show the regulatory role of IFN-γ on alveolar macrophage function.
Figure 9:
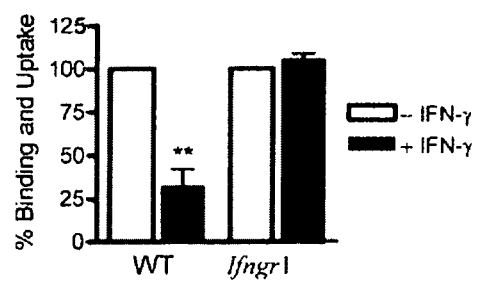
FIG. 9 shows the specific role of IFN-γ on alveolar macrophage bacterial uptake. Flow cytometric analysis of bacterial uptake by CD11c$^+$ BALF cells from C57BL/6 wild-type and Ifngr1$^{-/-}$ mice after overnight incubation with 10 ng/ml of IFN-γ. The results are expressed as the relative percentages of bacterial uptake normalized to values observed in the absence of IFN-γ. The data represent the mean±s.d of three independent experiments. ** is P<0.01, compared to IFN-γ-treated CD11c$^+$ BALF cells from Ifngr1$^{-/-}$ mice (paired t-test).

To directly determine the influence of IFN-γ, exogenous IFN-γ was incubated with isolated alveolar macrophages or inoculated intranasally into naïve mice. It was found that exposure to IFN-γ inhibited alveolar macrophage-mediated phagocytosis of pneumococci both in vitro and in vivo (FIG. 4A and FIG. 9). Furthermore, inoculation of exogenous IFN-γ was found to mimic viral infection in that it led to similar decreases in initial bacterial clearance (FIG. 4B). Further analysis of the CD11c$^+$ cell population showed that IFN-γ treatment suppressed surface expression of the class A scavenger receptor MARCO (FIG. 4C), a receptor responsible for phagocytosis of unopsonized pneumococci by alveolar macrophages (Arredouani et al., "The Scavenger Receptor MARCO is Required for Lung Defense Against Pneumococcal Pneumonia and Inhaled Particles," *J Exp Med* 200:267-72 (2004), which is hereby incorporated by reference in its entirety). As such, the MARCO-specific antibody ED31 blocked binding and uptake of pneumococci (FIG. 4D). Conversely, IFN-γ increased surface expression of MHCII (FIG. 4C). Thus, in agreement with previous reports (Speert et al., "Suppression by Human Recombinant Gamma Interferon of In Vitro Macrophage Nonopsonic and Opsonic Phagocytosis and Killing *Infect Immun* 59:1893-8 (1991), Lundborg et al., "Ingested Aggregates of Ultrafine Carbon Particles and Interferon-Gamma Impair Rat Alveolar Macrophage Function," *Environ Res* 81:309-15 (1999), which are hereby incorporated by reference in their entirety), these results demonstrate that IFN-γ inhibits bacterial phagocytosis by alveolar macrophages and suppresses innate defense against pneumococcal infection.

Figure 5:
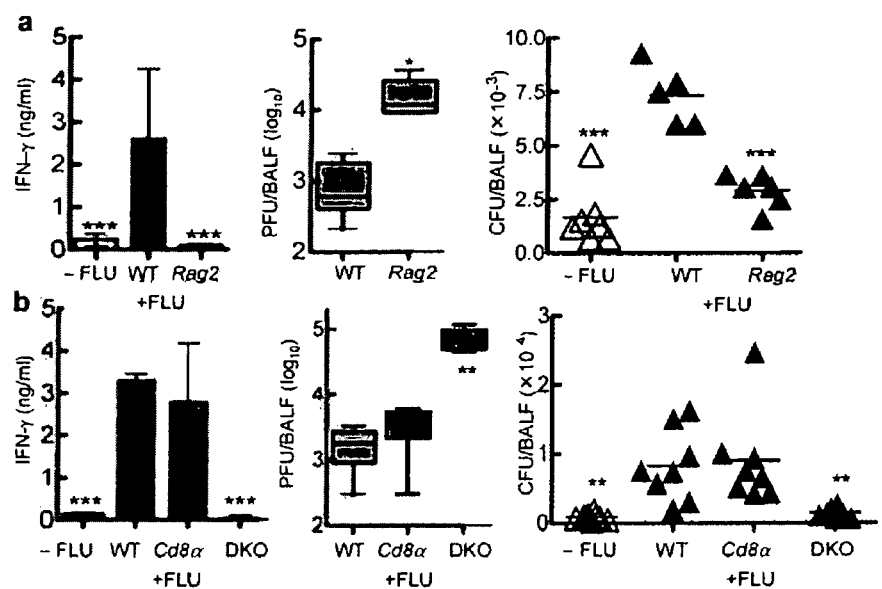
FIGS. 5A-B show T cell activation following influenza virus infection inhibits initial bacterial clearance in the lung (FIGS. 5A-B). IFN-γ levels (left), viral PFU (middle), and bacterial CFU (right) in the BALF of naïve mice and C57BL/6 WT and Rag2$^{-/-}$ mice 8 d after influenza infection (FIG. 5A) or C57BL/6 WT, Cd8a$^{-/-}$ and CD4-depleted Cd8a$^{-/-}$ (DKO) mice 8 d after influenza infection (FIG. 5B) 4 h after infection with 1×10$^5$ CFUs of A66.1 S. pneumoniae. Naïve WT, Rag2$^{-/-}$ and Cd8$^{-/-}$ mice infected only with S. pneumoniae are presented together (FLU). * is P<0.05,  is P<0.01 , * is P<0.001, compared to influenza-infected WT mice. The data are composite results of two independent experiments.
Figure 10:
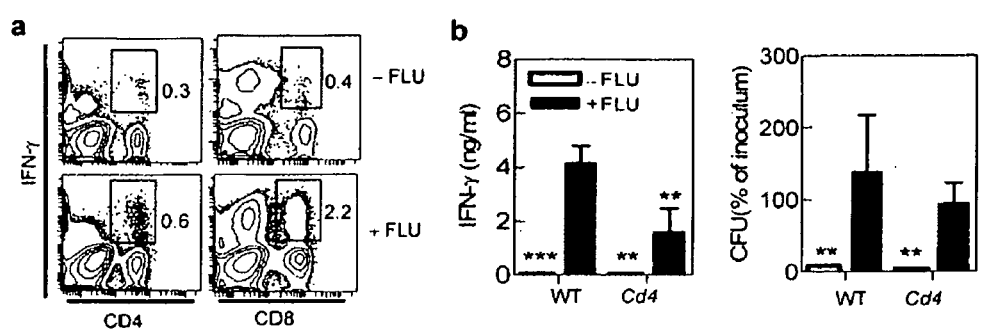
FIGS. 10A-B show influenza-induced T cell IFN-γ expression in the lung.
As shown in FIG. 10C, the levels of IFN-γ (left) and bacterial CFU (right) in BALF 4 hr after pneumococcal infection show that in the absence of CD4$^+$ T cells, there is still sufficient IFN-γ production in influenza-infected mice to inhibit 4 hr clearance of pneumococci.  is P<0.01 and * is P<0.001, relative to influenza infected wild-type mice.

CD4$^+$ and CD8$^+$ T cells are the major pulmonary cell types that produce IFN-γ after influenza infection (Swain et al., "T Cell Responses to Influenza Virus Infection: Effector and Memory Cells," *Viral Immunol* 17:197-209 (2004), which is hereby incorporated by reference in its entirety and FIG. 10A) and IFN-γ expression is diminished in Rag2$^{-/-}$ mice (FIG. 5A) as well as CD4-depleted Cd8a$^{-/-}$ mice (FIG. 5B). In agreement with the generally accepted concept that T cells are important for anti-viral protection (Swain et al., "T Cell Responses to Influenza Virus Infection: Effector and Memory Cells," *Viral Immunol* 17:197-209(2004), which is hereby incorporated by reference in its entirety), there was a >10-fold viral burden in the respiratory tracts of T cell-deficient mice eight days post-influenza infection (FIG. 5A-B). Interestingly, initial bacterial clearance in these mice was not inhibited (FIG. 5A-B). These results indicate that the defective bacterial clearance seen in viral-infected mice does not correlate with lung viral burden but is correlated with IFN-γ expression. Of note, IFN-γ production by either CD4$^+$ or CD8$^+$ T cells alone was sufficient to inhibit initial bacterial clearance (FIG. 5B and FIG. 10B). Previous studies have shown that IFN-γ has a minimal role in viral clearance (La Gruta et al., "A Question of Self-Preservation: Immunopathology in Influenza Virus Infection," *Immunol Cell Biol* 85:85-92 (2007), Brown et al., "CD4 T Cell-Mediated Protection from Lethal Influenza: Perforin and Antibody-Mediated Mechanisms Give a One-Two Punch,"*J Immunol* 111, 2888-98 (2006), which are hereby incorporated by reference in their entirety) and similarly, IFN-γR deficient humans show only moderate susceptibility to viral infections (Carneiro-Sampaio et al., "Immunity to Microbes: Lessons from Primary Immunodeficiencies," *Infect Immun* (2007), which is hereby incorporated by reference in its entirety). Thus, while the protective role of T cells in influenza infection appears to be IFN-γ-independent, pulmonary expression of IFN-γ significantly suppresses innate immunity that is required for effective clearance of extracellular pathogens.

Example 4

IFN-γ Neutralization Restores Pulmonary Innate Defense

Figure 6:
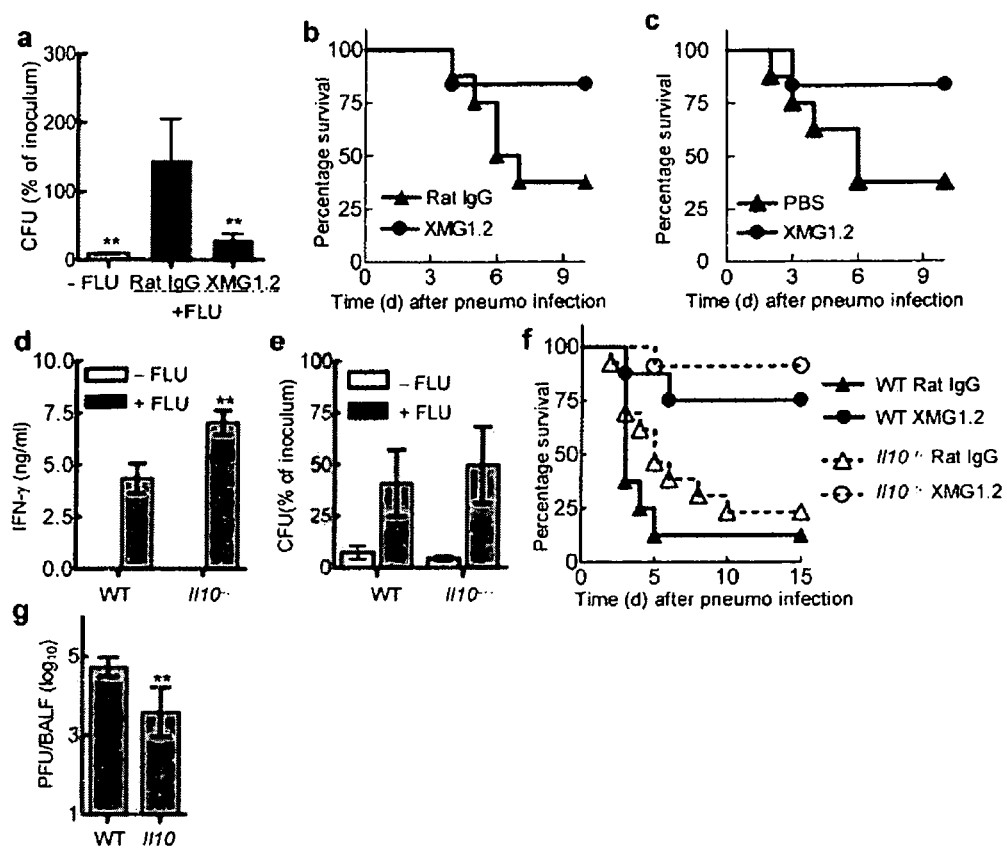
FIGS. 6A-G show IFN-γ neutralization following viral infection restores innate immunity to pneumococci.
Figure 11:
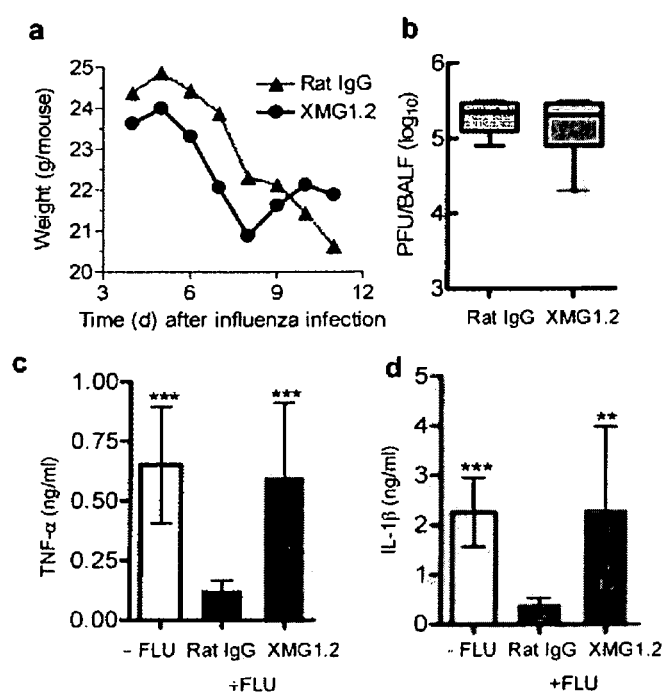
FIGS. 11A-D show IFN-γ neutralization following viral infection.
Figure 12:
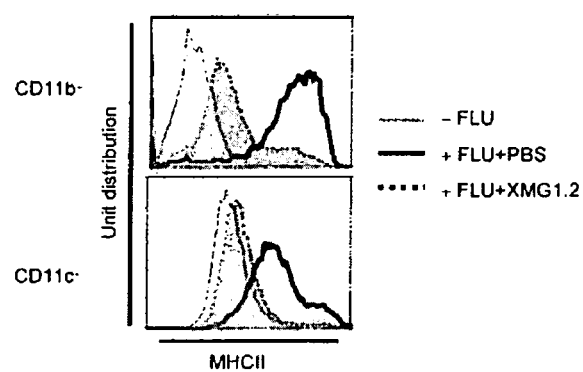
FIG. 12 shows flow cytometry of BALF cells for MHCII expression after influenza infection. MHCII expression is analyzed on CD11b$^+$ (top) and CD11c$^+$ (bottom) BALF cells from C57BL/6 mice following i.p. treatment with XMG1.2 anti-IFN-γ mAb or PBS after viral infection. The data are representative of four mice per group.

Experiments were next conducted to determine whether increased susceptibility to pneumococcal infection could be prevented by IFN-γ neutralization. It was found that in vivo treatment with IFN-γ-specific antibody XMG1.2 had little effect on the course of viral infection (FIG. 11A-B). However, macrophage expression of inflammatory cytokines such as TNF-α and IL-1β following bacterial infection was suppressed by previous viral infection but intranasal XMG1.2 treatment reversed this suppression (FIG. 11C-D). In addition, XMG1.2 treatment prevented upregulation of MFICII expression on both CD11c$^+$ and CD11b$^+$ cell populations (FIG. 12). Remarkably, early bacterial clearance in the treated mice was restored (FIG. 6A) and both C57BL/6 and BALB/c mice showed enhanced resistance to Lethal pneumococcal challenge (FIG. 6B-C). The results imply that production of IFN-γ following influenza infection alters the activation status of local macrophages, allowing them to enhance adaptive anti-viral responses through increased MHC expression while repressing their ability to mediate innate immunity. It has been reported that IFN-γ suppresses the phagocytic activity of dendritic cells while stimulating their antigen presentation functions (Mellman et al., "Dendritic Cells: Specialized and Regulated Antigen Processing Machines," *Cell* 106:255-8 (2001), which is hereby incorporated by reference in its entirety). Thus, alveolar macrophages appear to have some properties in common with dendritic cells.

Earlier studies reported that IL-10 plays an important role in mediating susceptibility to secondary bacterial infection (van der Sluijs et al., "IL-10 is An Important Mediator of the Enhanced Susceptibility to Pneumococcal Pneumonia After Influenza Infection," *J Immunol* 172:7603-9 (2004), van der Sluijs et al, "Influenza-Induced Expression of Indoleamine 2,3-Dioxygenase Enhances Interleukin-10 Production and Bacterial Outgrowth During Secondary Pneumococcal Pneumonia," *J Infect Dis* 193:214-22 (2006), which are hereby incorporated by reference in their entirety). Thus, Il10$^{-/-}$ mice were used to examine a possible connection between IL-10 and IFN-γ in synergistic microbial infections. Il10$^{-/-}$ mice produced increased levels of IFN-γ after viral infection (FIG. 6D). However, there was no significant difference between WT and Il10$^{-/-}$ mice in initial bacterial clearance (FIG. 6E). Most importantly, neutralization of IFN-γ equally protected WT and Il10$^{-/-}$ mice from secondary bacterial infection, indicating a fundamental role of IFN-γ in mediating susceptibility independent of IL-10 (FIG. 6F). It is of interest that Il10$^{-/-}$ mice cleared viral infection more effectively than WT animals (FIG. 6G), suggesting that, in turn, the kinetics of susceptibility to bacterial infection may differ somewhat in the absence of IL-10.

The innate immune system in the airways is well-developed, consisting of both nonspecific defenses and a cellular component that consists almost entirely of alveolar macrophages. It has been found that alveolar macrophages play an essential role in initial clearance of pneumococci within the respiratory tract. This macrophage-mediated antibacterial defense was inhibited during the recovery stage of influenza infection and, consequently, led to a high susceptibility to pneumococcal infection. However, bacterial clearance activity remained high in influenza-infected Ifng$^{-/-}$ and Ifngr1$^{-/-}$ mice, as well as in T cell deficient mice. In addition, exogenous IFN-γ treatment mimicked viral infection, and IFN-γ blockade following viral infection restored innate macrophage responses and increased survival after secondary pneumococcal challenge. It is concluded that IFN-γ produced in the respiratory tract following viral infection suppresses alveolar macrophage-mediated protection against pulmonary pneumococcal infection. IFN-γ seems to downregulate the expression of MARCO phagocytic receptor.

Efficient pulmonary bacterial clearance was observed in naive mice 4 h after infection with relatively low inoculum doses of pneumococci ($10^4$-$10^5$ CFU), at a time preceding neutrophil influx into the lungs. However, at larger inoculum doses (>$10^6$ CFU), the ability of the mice to clear infection was overwhelmed and the animals died within a few days. Since most previous studies have focused on later stages of pneumococcal infection (24 h or later), when there is bacterial outgrowth followed by an influx of neutrophils into the lung and an intense inflammatory response (van der Sluijs et al., "IL-10 is an Important Mediator of the Enhanced Susceptibility to Pneumococcal Pneumonia After Influenza Infection," *J Immunol* 172:7603-9 (2004), Couch, R. B., "The Effects of Influenza on Host Defenses," *J Infect Dis* 144:284-91 (1981), which are hereby incorporated by reference in their entirety), the critical role of alveolar macrophages has often been overlooked. By examining very early events in response to low bacterial challenge doses, the studies presented here have been able to define the tight regulation between innate and adaptive immunity in the pulmonary tract and the basis for increased susceptibility to *S. pneumoniae* following influenza infection.

Potential mechanisms involved in synergy between influenza virus and *S. pneumoniae* have been summarized in two reviews (Couch, R. B., "The Effects of Influenza on Host Defenses," *J Infect Dis* 144:284-91 (1981), McCullers, J. A., "Insights Into the Interaction Between Influenza Virus and Pneumococcus," *Clin Microbiol Rev* 19:571-82 (2006), which are hereby incorporated by reference in their entirety). Among the various mechanisms proposed has been damage to the epithelial cell barrier by viral infection, providing increased attachment sites for the bacteria. However, lung inflammation typically tends to subside by the time of viral clearance (Nugent et al., "Tracheal Function During Influenza Infections," *Infect Immun* 42:1102-8 (1983), Hayden et al, "Local and Systemic Cytokine Responses During Experimental Human Influenza A Virus Infection, Relation to Symptom Formation and Host Defense," *J Clin Invest* 101:643-9 (1998), Kaiser et al., "Symptom Pathogenesis During Acute Influenza: Interleukin-6 and Other Cytokine Responses," *J Med Virol* 64:262-8 (2001), which are hereby incorporated by reference in their entirety), at the time of greatest susceptibility to pneumococcal infection. Viral strains that cause minimal epithelial cell damage still enhance susceptibility to subsequent bacterial infection (van der Sluijs et al., "Involvement of the Platelet-Activating Factor Receptor in Host Defense Against *Streptococcus Pneumoniae* During Postinfluenza Pneumonia," *Am J Physiol Lung Cell Mol Physiol* 290:L194-9 (2006), McCullers et al., "Role of Neuraminidase in Lethal Synergism Between Influenza Virus and *Streptococcus Pneumoniae*" *J Infect Dis* 187:1000-9 (2003), which are hereby incorporated by reference in their entirety). Furthermore, in the studies using T-deficient animals, there was an inverse relationship between viral burden and bacterial clearance. Although IFN-γ is not required for efficient viral clearance (Price et al., "The Role of Alpha/Beta and Gamma Interferons in Development of Immunity to Influenza A Virus in Mice," *J Virol* 74:3996-4003 (2000), which is hereby incorporated by reference in its entirety), its presence during influenza infection may actually ameliorate the severity of inflammation and lung damage (Wiley et al., "Production of Interferon-Gamma by Influenza Hemagglutinin-Specific CD8 Effector T Cells Influences the Development of Pulmonary Immunopathology," *Am J Pathol* 158:119-30 (2001), which is hereby incorporated by reference in its entirety). Influenza neuraminidase and up-regulation of platelet-activating factor receptor expression during viral infection has been reported to increase bacterial adherence (van der Sluijs et al., "Involvement of the Platelet-Activating Factor Receptor in Host Defense Against *Streptococcus Pneumoniae* During Postinfluenza Pneumonia," *Am J Physiol Lung Cell Mol Physiol* 290:L194-9 (2006), McCullers et al, "Lethal Synergism Between Influenza Virus and *Streptococcus Pneumoniae*: Characterization of a Mouse Model and the Role of Platelet-Activating Factor Receptor," *J Infect Dis* 186:341-50 (2002), which are hereby incorporated by reference in their entirety), although treatment of mice with a competitive antagonist of platelet-activating factor receptor was found to have no influence on survival rates (McCullers et al., "Lethal Synergism Between Influenza Virus and *Streptococcus Pneumoniae*: Characterization of a Mouse Model and the Role of Platelet-Activating Factor Receptor," *J Infect Dis* 186:341-50 (2002), which is hereby incorporated by reference in its entirety). IL-10 expression induced by 2,3-dioxygenase in influenza virus-infected hosts has been reported to be partially responsible for susceptibility (van der Sluijs et al., "IL-10 is an Important Mediator of the Enhanced Susceptibility to Pneumococcal Pneumonia after Influenza Infection," *J Immunol* 172:7603-9 (2004), van der Sluijs et al., "Influenza-Induced Expression of Indoleamine 2,3-dioxygenase Enhances Interleukin-10 Production and Bacterial Outgrowth During Secondary Pneumococcal Pneumonia," *J Infect Dis* 193:214-22 (2006), which is hereby incorporated by reference in its entirety). Significant differences were not observed between WT and Il10$^{-/-}$ mice in this regard although Il10$^{-/-}$ mice cleared virus more effectively than WT animals. Thus, the kinetics of susceptibility to bacterial infection may be shifted in Il10$^{-/-}$ mice compared to WT mice, possibly explaining the observed small differences at any given time point after viral infection. In any case, the ability of IFN-γ to mediate susceptibility to secondary bacterial infection is IL-10-independent, as IFN-γ neutralization equally protected IL-10$^{-/-}$ mice and WT mice. Finally, it has been reported that considerable neutrophil dysfunction occurs in the lungs mice double infected with influenza virus and pneumococcus (Craft et al., "Effect of Virus Infections on Polymorph Function in Children," *Br Med J* 1:1570 (1976), Abramson et al., "Polymorphonuclear Leukocyte Dysfunction During Influenza Virus Infection in Chinchillas," *J Infect Dis* 143: 836-45 (1981), McNamee et al., "Both Influenza-Induced Neutrophil Dysfunction and Neutrophil-Independent Mechanisms Contribute to Increased Susceptibility to a Secondary *Streptococcus Pneumoniae* Infection," *Infect Immun* 74:6707-21 (2006), which are hereby incorporated by reference in their entirety. However, the timing of this dysfunction does not necessarily correlate with increased susceptibility to bacterial infection (McNamee et al., "Both Influenza-Induced Neutrophil Dysfunction and Neutrophil-Independent Mechanisms Contribute to Increased Susceptibility to a Secondary *Streptococcus Pneumoniae* Infection," *Infect Immun* 74:6707-21 (2006), which is hereby incorporated by reference in its entirety). Furthermore, as shown in the present invention, neutrophils do not appear to play a major role in initial bacterial clearance. Nevertheless, the possibility that viral infection may inhibit the overall bacterial killing capacity of neutrophils at later stages of bacterial infection and contribute to susceptibility to secondary bacterial infection cannot be excluded. It was recently shown that sustained desensitization to bacterial Toll-like receptor ligands after resolution of respiratory influenza infection resulted in lower TNF-α production by alveolar macrophages, which contributed to secondary bacterial infection due to reduced neutrophil recruitment (Didierlaurent et al., "Sustained Desensitization to Bacterial Toll-like Receptor Ligands After Resolution of Respiratory Influenza Infection," *J Exp Med* 205:323-9 (2008), which is hereby incorporated by reference in its entirety). Thus, dampening of TLR signaling may also be involved in IFN-γ mediated inhibition of alveolar macrophage function. Although these results have demonstrated a fundamental role for IFN-γ in enhancing susceptibility to secondary bacterial infection, it should be noted that there may be additional contributing factors, because even after IFN-γ blockade, small increases in bacterial burden and a degree of lethality were still observed.

Alveolar macrophages are known to suppress induction of adaptive immunity by inhibiting dendritic cell function (Holt et al., "Downregulation of the Antigen Presenting Cell Function(s) of Pulmonary Dendritic Cells In Vivo by Resident Alveolar Macrophages, *J Exp Med* 177:397-407 (1993), Thepen et al., "Alveolar Macrophages Down-Regulate Local Pulmonary Immune Responses Against Intratracheally Administered T-Cell-Dependent, but Not T-Cell-Independent Antigens," *Immunology* 76:60-4 (1992), Thepen et al., "Alveolar Macrophage Elimination In Vivo is Associated with an Increase in Pulmonary Immune Response in Mice," *J Exp Med* 170:499-509 (1989), Iwasaki, A., "Mucosal Dendritic cells," *Annu Rev Immunol* 25:381-418 (2007), which are hereby incorporated by reference in their entirety). Their inactivation on day seven of influenza infection may be a mechanism that evolved to allow enhanced induction of specific anti-influenza immune memory (Bot et al., "Protective Role of Gamma Interferon During the Recall Response to Influenza Virus," *J Virol* 72:6637-45 (1998), which is hereby incorporated by reference in its entirety), albeit at the temporary expense of innate protection against bacteria pathogens such as *S. pneumoniae*. This concept agrees with early studies that identified dysfunctional pulmonary macrophage function after influenza infection (Kodihalli et al., "Effect of Avian Influenza Virus Infection on the Phagocytic Function of Systemic Phagocytes and Pulmonary Macrophages of Turkeys," *Avian Dis* 38:93-102 (1994), Jakab, G. J., "Immune Impairment of Alveolar Macrophage Phagocytosis During Influenza Virus Pneumonia," *Am Rev Respir Dis* 126:778-82 (1982), which are hereby incorporated by reference in their entirety). The results indicate that the cells responsible for this effect are infiltrating T cells that secrete high levels of IFN-γ. From a basic point of view, the results are consistent with a recent report regarding the ability of T cells to temper initial innate responses to inflammatory stimuli (Kim et al., "Adaptive Immune Cells Temper Initial Innate Responses," *Nat Med* 13:1248-1252 (2007), Palm et al., "Not So Fast: Adaptive Suppression of Innate Immunity," *Nat Med* 13:1142-4 (2007), which are hereby incorporated by reference in their entirety), although the precise mechanisms responsible for the two effects may be dissimilar. In contrast to acute viral infection examined in this invention, chronic viral infection was reported to induce prolonged production of low levels of IFN-γ and systemic activation of macrophages, resulting in up-regulation of the basal activation state of innate immunity against subsequent bacterial infections (Barton et al., "Herpesvirus Latency Confers Symbiotic Protection from Bacterial Infection," *Nature* 447:326-9 (2007), which is hereby incorporated by reference in its entirety).

Overall, the results show that IFN-γ that is induced during the recovery phase of influenza alters alveolar macrophage functions to facilitate generation of adaptive immunity but simultaneously, causes a decrease in MARCO-mediated innate immunity and enhanced susceptibility to secondary bacterial infection. Of note, diminished alveolar macrophage MARCO expression has also been observed in human patients treated with aerosolized IFN-γ (Raju B. et al., "Aerosolized Gamma Interferon (IFN-gamma) Induces Expression of the Genes Encoding the IFN-Gamma-Inducible 10-Kilodalton Protein but Not Inducible Nitric Oxide Synthase in the Lung During Tuberculosis," *Infect Immun* 72:1275-83 (2004), which is hereby incorporated by reference in its entirety). The fact that IFN-γ neutralization can reverse these effects may provide a new therapeutic approach for protecting the human population from secondary bacterial infections during influenza pandemics.

Figure 13:
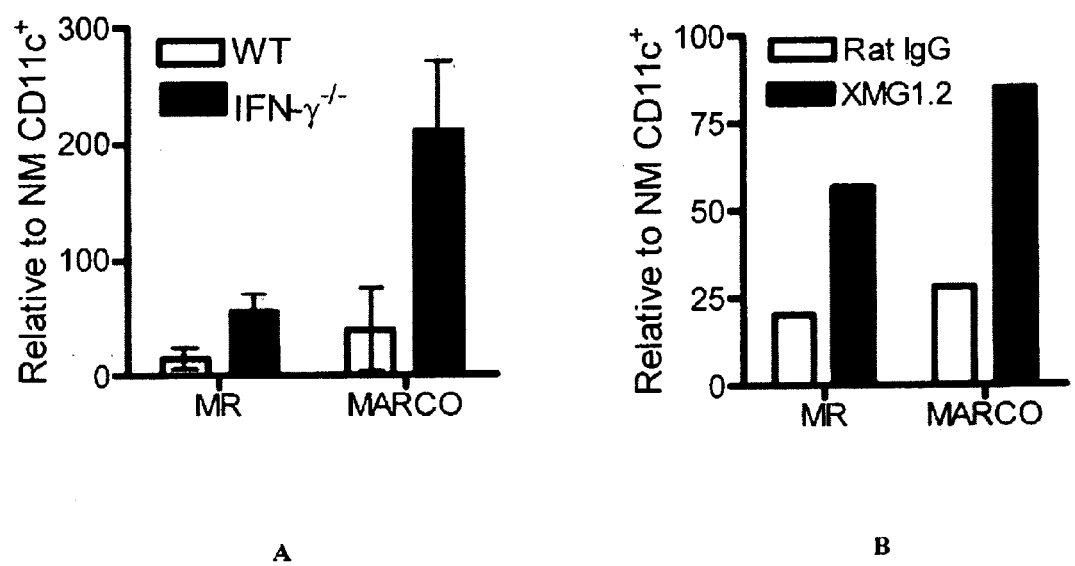
FIGS. 13A-B show the relative transcription levels of the mannose receptor (MR) and MARCO in CD11c+ alveolar macrophages during recovery from influenza infection.

FIG. 13A-B shows expression of MARCO following influenza infection and the role of IFN-γ. Earlier results (see FIG. 4) showed the direct effect of IFN-γ on MARCO expression, not the influence of influenza infection on MARCO. Also, FIG. 13 depicts the suppressive effect of influenza infection on expression of a second scavenger receptor, the mannose receptor, which likely plays an important role in innate immune defense to other pathogens (other than pneumococci).

Figure 14:
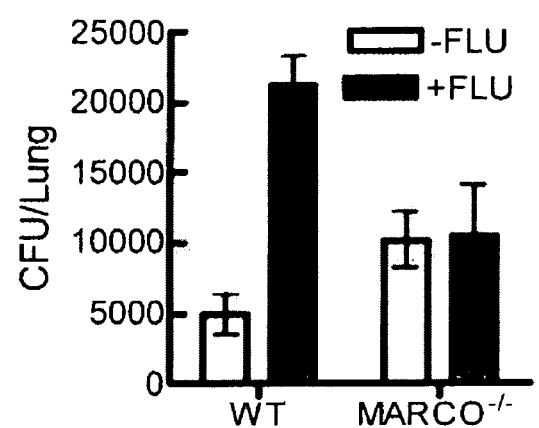
FIG. 14 shows bacterial CFU in the lungs of naïve and day 8 postinfluenza infected C57BL/6 WT and MARCO–/– mice 4 hr after infection with $10^5$ CFU of S. pneumoniae.

FIG. 14 shows the use of MARCO KO mice. Clearance of pneumococci is decreased in the absence of MARCO (already known from the published work of others), but FIG.

14 shows that prior influenza infection has no effect on clearance that occurs in these mice, i.e., in the absence of MARCO.

Figure 15:
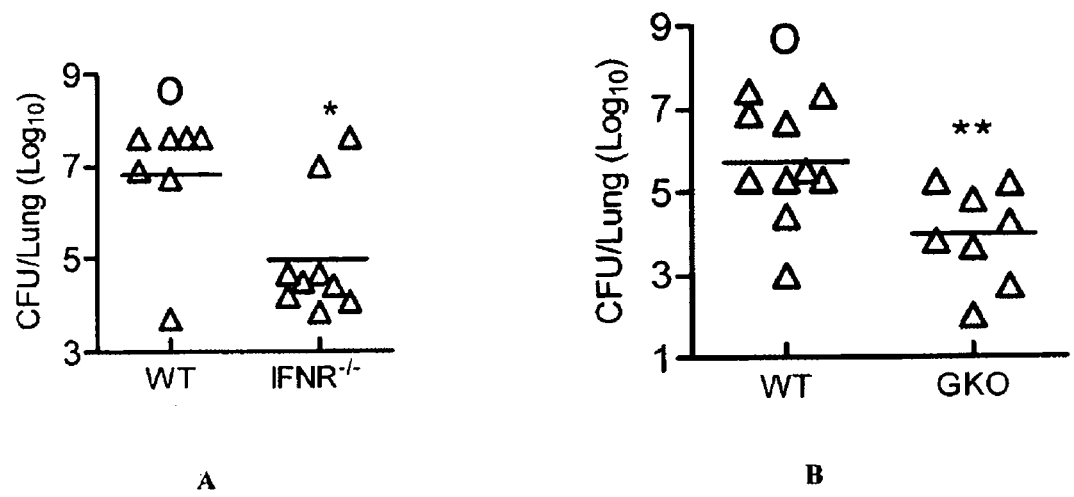
FIGS. 15 A-B show impaired 48 hr bacterial clearance following Influenza infection. C57BL/6 WT IFN-γR–/– and IFN-g–/– mice were infected intranasally with 50 PFU of A/PR/8/34 (H1N1) influenza virus followed by infection with $10^5$ CFU of D39 S. pneumoniae. Numbers of bacteria (mean±s.d) at 48 hr in the lung are shown. Both WT and KO mice were infected with pneumococci on day 12 after influenza infection when there was no detectable virus remaining in the lungs. O=dead mice. * is P<0.05 and ** is P<0.01 relative to influenza infected WT mice.

FIGS. 15A-B shows the clearance of pneumococci at 48 hr and the role of IFN-γ. Data has also been presented on very early pneumococcal clearance (4 hr after bacterial challenge) and increased death of mice previously infected with flu. It has now been determined that defective pneumococcal clearance was still observed 48 hr after bacterial challenge in flu-infected mice, suggesting that the increased death previously observed was in fact due to bacterial outgrowth rather than simply a heightened inflammatory response following flu.

Figure 16:
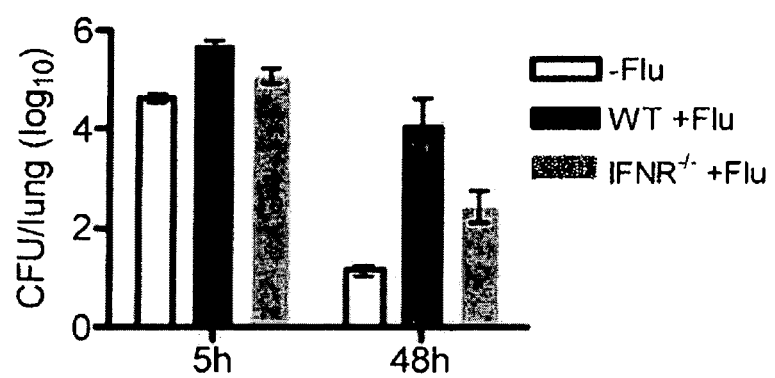
FIG. 16 shows influenza infection impairs pulmonary clearance of methicillin-resistant *Staphylococcus aureus* (MRSA), in part due to IFN-γ production. C57BL/6 WT and IFN-γ receptor KO (IFNR−/−) mice were infected intranasally with 50 PFU of A/PR/8/34 (H1N1) influenza virus followed by infection with $10^6$ CFU of MRSA (strain USA200). —Flu is WT mice not infected with influenza but challenged with MRSA. Numbers of bacteria (mean±s.d) at 5 and 48 hr in the lung are shown. Both WT and KO mice were infected with *S. aureus* on day 12 after influenza infection when there was no detectable virus remaining in the lungs.

FIG. 16 shows the defective clearance of methicillin-resistant *Staphylococcus aureus* (MRSA) following influenza and the importance of IFN-γ. Previous results concerned only pneumococcus infection. It has now been found that mice also have heightened susceptibility to MRSA and this is mediated in part by IFN-γ. Hospital- and community-acquired MRSA is a significant and growing health problem in the United States.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of protecting a subject with a respiratory tract viral infection against developing a subsequent bacterial infection in the subject's lungs, said method comprising:

selecting a subject with a respiratory tract viral infection who is susceptible to bacterial infection in the lungs as a result of production of interferon-gamma (IFNγ) in the subject's lungs, said subject being in contact with said bacteria, wherein said bacteria is selected from the group consisting of *S. pneumoniae, H. influenzae, S. aureus, M. catarrhalis, P. carinii, S. pyogenes,* and *P. aeruginosa*;

providing a therapeutic agent that inhibits IFNγ; and administering the therapeutic agent to the selected subject under conditions effective to protect against a bacterial infection in the lungs as a result of production of interferon-gamma (IFNγ) in the subject's lungs, wherein said bacterial infection is caused by a bacteria selected from the group consisting of *S. pneumoniae, H. influenzae, S. aureus, M. catarrhalis, P. carinii, S. pyogenes,* and *P. aeruginosa*.

2. The method of claim 1, wherein the selected subject is human.

3. The method of claim 1, wherein said administering is carried out orally, intranasally, subcutaneously, intravenously, intramuscularly, parenterally, intraperitoneally, by application to the mucous membranes, or by inhalation.

4. The method according to claim 1, wherein the therapeutic agent that inhibits IFNγ binds to IFNγ.

5. The method according to claim 1, wherein the therapeutic agent that inhibits IFNγ binds to the IFNγ-receptor.

6. The method according to claim 1, wherein the therapeutic agent is selected from the group consisting of an anti-IFNγ antibody or fragment thereof which binds to the IFNγ receptor, a soluble IFNγ receptor, a hybrid IFNγ receptor molecule, and an anti-IFNγ receptor antibody.

* * * * *